(12) United States Patent
Tan et al.

(10) Patent No.: US 8,170,656 B2
(45) Date of Patent: May 1, 2012

(54) WEARABLE ELECTROMYOGRAPHY-BASED CONTROLLERS FOR HUMAN-COMPUTER INTERFACE

(75) Inventors: Desney Tan, Kirkland, WA (US); T. Scott Saponas, Seattle, WA (US); Dan Morris, Bellevue, WA (US); Jim Turner, Monroe, WA (US)

(73) Assignee: Microsoft Corporation, Redmond, WA (US)

( * ) Notice: Subject to any disclaimer, the term of this patent is extended or adjusted under 35 U.S.C. 154(b) by 427 days.

(21) Appl. No.: 12/404,223

(22) Filed: Mar. 13, 2009

(65) Prior Publication Data

US 2009/0326406 A1 Dec. 31, 2009

Related U.S. Application Data

(63) Continuation-in-part of application No. 12/146,471, filed on Jun. 26, 2008.

(51) Int. Cl.
- G06F 3/033 (2006.01)
- G09G 5/08 (2006.01)
- A61B 5/04 (2006.01)
- A61B 5/103 (2006.01)
- A61B 5/117 (2006.01)
- G01C 9/00 (2006.01)
- G01C 17/00 (2006.01)
- G01C 19/00 (2006.01)

(52) U.S. Cl. ........ 600/546; 345/157; 345/158; 600/372; 600/382; 600/384; 600/595; 702/150; 715/863

(58) Field of Classification Search .................. 345/157, 345/158; 600/372, 382, 384, 546, 595; 702/150; 715/863

See application file for complete search history.

(56) References Cited

U.S. PATENT DOCUMENTS

| | | | |
|---|---|---|---|
| 4,297,701 A * | 10/1981 | Henriques | 342/42 |
| 6,205,716 B1 * | 3/2001 | Peltz | 52/36.2 |
| 6,223,018 B1 * | 4/2001 | Fukumoto et al. | 455/41.1 |
| 6,244,873 B1 | 6/2001 | Hill et al. | |
| 6,636,763 B1 * | 10/2003 | Junker et al. | 600/545 |
| 6,643,541 B2 | 11/2003 | Mok et al. | |

(Continued)

OTHER PUBLICATIONS

"International Search Report", Mailed Date: Sep. 30, 2010, Application No. PCT/US2010/026699, Filed Date: Mar. 9, 2010, pp. 9.

(Continued)

*Primary Examiner* — Max Hlndenburg
*Assistant Examiner* — Sean Dougherty
(74) *Attorney, Agent, or Firm* — Lyon & Harr, LLP; Mark A. Watson

(57) ABSTRACT

A "Wearable Electromyography-Based Controller" includes a plurality of Electromyography (EMG) sensors and provides a wired or wireless human-computer interface (HCI) for interacting with computing systems and attached devices via electrical signals generated by specific movement of the user's muscles. Following initial automated self-calibration and positional localization processes, measurement and interpretation of muscle generated electrical signals is accomplished by sampling signals from the EMG sensors of the Wearable Electromyography-Based Controller. In operation, the Wearable Electromyography-Based Controller is donned by the user and placed into a coarsely approximate position on the surface of the user's skin. Automated cues or instructions are then provided to the user for fine-tuning placement of the Wearable Electromyography-Based Controller. Examples of Wearable Electromyography-Based Controllers include articles of manufacture, such as an armband, wristwatch, or article of clothing having a plurality of integrated EMG-based sensor nodes and associated electronics.

18 Claims, 9 Drawing Sheets

U.S. PATENT DOCUMENTS

| | | | |
|---|---|---|---|
| 6,720,984 B1 | 4/2004 | Jorgensen et al. | |
| 6,915,148 B2* | 7/2005 | Finneran et al. | 600/372 |
| 6,965,842 B2 | 11/2005 | Rekimoto | |
| 6,984,208 B2 | 1/2006 | Zheng | |
| 7,148,879 B2 | 12/2006 | Amento et al. | |
| 7,333,090 B2* | 2/2008 | Tanaka et al. | 345/158 |
| 7,554,549 B2* | 6/2009 | Sagar et al. | 345/473 |
| 7,565,295 B1* | 7/2009 | Hernandez-Rebollar | 704/271 |
| 2001/0041846 A1* | 11/2001 | Appel et al. | 600/546 |
| 2004/0024312 A1* | 2/2004 | Zheng | 600/437 |
| 2004/0068409 A1 | 4/2004 | Tanaka et al. | |
| 2006/0071934 A1* | 4/2006 | Sagar et al. | 345/473 |
| 2006/0079801 A1 | 4/2006 | DeLuca et al. | |
| 2006/0121958 A1 | 6/2006 | Jung et al. | |
| 2007/0140562 A1 | 6/2007 | Linderman | |
| 2008/0208030 A1* | 8/2008 | Finneran et al. | 600/393 |
| 2008/0211768 A1* | 9/2008 | Breen et al. | 345/157 |
| 2008/0288020 A1* | 11/2008 | Einav et al. | 607/48 |
| 2010/0069736 A1* | 3/2010 | Finneran et al. | 600/392 |

OTHER PUBLICATIONS

Guerreiro, et al., "EMG as a Daily Wearable Interface", Retrieved at <<http://vimmi.inesc-id.pt/publication.php?publication_id=126>>, Proceedings of the First International Conference on Computer Graphics Theory and Applications, Feb. 25-28, 2006, pp. 8.

Costanza, et al., "EMG as a Subtle Input Interface for Mobile Computing", Retrieved at <<http://web.media.mit.edu/~enrico/papers/EMG_mobileHCI.pdf>>, Apr. 1, 2003, pp. 5.

Barry, et al., "Acoustic and Surface EMG Diagnosis of Pediatric Muscle Disease", Retrieved at <<http://deepblue.lib.umich.edu/bitstream/2027.42/50149/1/880130403_ftp.pdf>>, Department of Physical Medicine and Rehabilitation, University of Michigan Medical Center, vol. 13, Issue 04, Apr. 1990, pp. 286-290.

"Biosemi", Retrieved at <<http://www.biosemi.com>>, Retrieved Date: Sep. 29, 2008, p. 1.

Burges, Christopher J.C., "A Tutorial on Support Vector Machines for Pattern Recognition", Retrieved at <<http://www.cs.princeton.edu/courses/archive/fall06/cos402/papers/SVM-tutorial>>, Data Mining and Knowledge Discovery, vol. 2, Issue 02, Jun. 1998, pp. 121-167.

Costanza, et al., "Toward Subtle Intimate Interfaces for Mobile Devices using an EMG Controller", Retrieved at <<http://delivery.acm.org/10.1145/1060000/1055039/p481-costanza.pdf?key1=1055039&key2=9922432221&coll=GUIDE&dl=GUIDE&CFID=3954844&CFTOKEN=94910745>>, Proceedings of the SIGCHI conference on Human factors in computing systems, 2005, pp. 481-489.

Costanza, et al., "Intimate Interfaces in Action: Assessing the Usability and Subtlety of EMG-Based Motionless Gestures", Retrieved at <<http://delivery.acm.org/10.1145/1250000/1240747/p819-costanza.pdf?key1=1240747&key2=7342432221&coll=GUIDE&dl=GUIDE&CFID=3955033&CFTOKEN=56619912>>, Proceedings of the SIGCHI conference on Human factors in computing systems, 2007, pp. 819-828.

Arieta, et al., "Development of a Multi-DOF Electromyography Prosthetic System using the Adaptive Joint Mechanism", Retrieved at <<http://www.robotcub.org/misc/review3/06_Hernandez_Kato_Yokai_Yu.pdf>>, vol. 3, Issue 02, 2006, pp. 1-10.

Jacobsen, et al., "Computational Requirements for Control of the Utah Arm", Retrieved at <<http://delivery.acm.org/10.1145/820000/810395/p149-jacobsen.pdf?key1=810395&key2=7713432221&coll=GUIDE&dl=GUIDE&CFID=3956097&CFTOKEN=49888308>>, ACM '74 Proceedings of the 1974 annual conference, vol. 1, 1974, pp. 149-155.

Jiang, et al., "A Method of Recognizing Finger Motion Using Wavelet Transform of Surface EMG Signal", Retrieved at <<http://ieeexplore.ieee.org/iel5/10755/33900/01617020.pdf>>, Proceedings of the International Conference of IEEE Engineering in Medicine and Biology Society, Jan. 17-18, 2006, pp. 2672-2674.

Kiguchi, et al., "Neuro-Fuzzy Control of a Robotic Exoskeleton with EMG Signals", Retrieved at <<http://ieeexplore.ieee.org/iel5/91/29260/01321076.pdf>>, IEEE Transactions on Fuzzy Systems, vol. 12, Issue 04, Aug. 2004, pp. 481-490.

"Kine Biomedical Engineering", Retrieved at <<http://www.kine.is>>, Retrieved Date: Sep. 29, 2008, p. 1.

Xu, et al., "An Improved Method for Muscle Activation Detection during Gait", Retrieved at <<http://ieeexplore.ieee.org/iel5/9317/29618/01345029.pdf?tp=&isnumber=&arnumber=1345029>>, Canadian Conference on Electrical and Computer Engineering, vol. 1, May 2-5, 2004, pp. 0357-0360.

Lee, et al., "Using a Low-Cost Electroencephalograph for task classification in HCI research", Retrieved at <<http://delivery.acm.org/10.1145/1170000/1166268/p81-lee.pdf?key1=1166268&key2=8193432221&coll=GUIDE&dl=GUIDE&CFID=4048572&CFTOKEN=21586596>>, Proceedings of the 19th annual ACM symposium on User interface software and technology, 2006, pp. 11.

Manabe, et al., "A Ring-Shaped EMG Measurement System for Applying to User Interface", Retrieved at <<http://ieeexplore.ieee.org/iel5/9009/28600/01280776.pdf?tp=&isnumber=&arnumber=1280776>>, Proceedings of the 25th Annual International Conference of the IEEE Engineering in Medicine and Biology Society, vol. 4, Sep. 17-21, 2003, pp. 3020-3023.

Mandryk, et al., "A Continuous and Objective Evaluation of Emotional Experience with Interactive Play Environments", Retrieved at <<http://delivery.acm.org/10.1145/1130000/1124926/p1027-mandryk.pdf?key1=1124926&key2=7114432221&coll=GUIDE&dl=GUIDE&CFID=4048858&CFTOKEN=92046935>>, Proceedings of the SIGCHI conference on Human Factors in computing systems, Feb. 15, 2006, pp. 1027-1036.

Naik, et al., "Hand Gestures for HCI using ICA of EMG", Retrieved at <<http://delivery.acm.org/10.1145/1280000/1273397/p67-naik.pdf?key1=1273397&key2=7224662221&coll=portal&dl=ACM&CFID=4425797&CFTOKEN=23141831>>, Proceedings of the HCSNet workshop on Use of vision in human-computer interaction, vol. 56, Nov. 2006, pp. 67-72.

Peleg et al., "Classification of Finger Activation for use in a Robotic Prosthesis Arm", Retrieved at <<http://ieeexplore.ieee.org/iel5/7333/26464/01178099.pdf?tp=&isnumber=&arnumber=1178099>>, IEEE Transactions on Neural Systems and Rehabilitation Engineering, vol. 10, Issue 04, Dec. 2002, pp. 290-293.

Platt, John C., "Sequential Minimal Optimization: A fast algorithm for training support vector machines", Retrieved at <<http://research.microsoft.com/usersiplatt/smoTR.pdf>>, Apr. 21, 1998, pp. 1-21.

Reaz, et al., "Techniques of EMG Signal Analysis: Detection, Processing, Classification, and Applications", Retrieved at <<http://www.biologicalprocedures.com/bpo/arts/1/115/m115.pdf>>, Biological Procedures Online, vol. 8, Issue 01, Mar. 23, 2006, pp. 11-35.

Schieber, Marc H., "Muscular Production of Individual Finger Movements: The Roles of Extrinsic Finger Muscles", Retrieved at <<http://www.jneurosci.org/cgi/reprint/15/1/284.pdf>>, The Journal of Neuroscience, Jan. 1995, pp. 284-297.

Wheeler, et al., "Gestures as Input: Neuroelectric Joysticks and Keyboards", Retrieved at <<http://ieeexplore.ieee.org/iel5/7756/27106/01203754.pdf>>, IEEE Pervasive Computing, vol. 2, Issue 02, Apr.-Jun. 2003, pp. 56-61.

Witten, et al., "Data Mining: Practical Machine Learning Tools and Techniques", Retrieved at <<http://www.team509.com/download/docs/Al/data%20mining/Morgan.Kaufmann.Data.Mining.Practical.Machine.Learning.Tools.and.Techniques.Second.Edition.Jun.2005.eBook-DDU.pdf>>, Newsletter ACM SIGMOD Record, vol. 31, Issue 01, Mar. 2002, pp. 558.

"Delsys system", Retrieved at <<http://www.delsys.com/Products/Wireless.html>>, Retrieved Date: Sep. 30, 2008, pp. 2.

"Activemg", Retrieved at <<http://www.futurehealth.org/wireless_emg.htm>>, Retrieved Date: Sep. 30, 2008, pp. 2.

"Kine Motion", Retrieved at <<http://www.kine.is/index.php?module=News&catid=&topic=4>>, Retrieved Date: Sep. 30, 2008, pp. 5.

Hartmann, et al., "Computer keyboard and mouse as a reservoir of pathogens in intensive care unit", Journal of Clinical Monitoring and Computing, vol. 18, Issue 01, Feb. 2004. pp. 7-12.

Moseley, et al., "EMG analysis of the scapular muscles during a shoulder rehabilitation program", Retrieved at <<http://www.udel.edu/PT/PT%20Clinical%20Services/journalclub/sojc/98_99/oct98/moseley.pdf>>, The American Journal of Sports Medicine, vol. 20, Issue 02, pp. 128-134.

Chen, X., X. Zhang, Z.-Y. Zhao, J.-H. Yang, V. Lantz, K.-Q. Wang, Hand gesture recognition research based on surface EMG sensors and 2D-accelerometers, 11th IEEE Int'l Symposium on Wearable Computers, Oct. 11-13, 2007, Boston, MA, USA.

Chen, X., X. Zhang, Z.-Y. Zhao, J.-H. Yang, V. Lantz, K.-Q. Wang, Multiple hand gesture recognition based on surface EMG signal, 1st Int'l Conf. on Bioinformatics and Biomedical Eng'g, Jul. 2007, pp. 506-509.

Makino, Y., H. Shinoda, Comfortable wristband interface measuring myoelectric pattern, Second Joint EuroHaptics Conf. and Symposium on Haptic Interfaces for Virtual Environment and Teleoperator Sys's., Mar. 2007, pp. 433-438, Tsukuba, Japan.

Wheeler, K. R., M. H. Chang, K. H. Knuth, Gesture-based control and EMG decomposition, IEEE Transactions on Sys's, Man, and Cybernetics, Part C: Applications and Reviews, Jul. 2006, vol. 36, No. 4, pp. 503-514.

Wong, Lut, U.S. Office Action, U.S. Appl. No. 12/146,471, Nov. 29, 2011.

* cited by examiner

WEARABLE ELECTROMYOGRAPHY-BASED CONTROLLERS FOR HUMAN-COMPUTER INTERFACE

CROSS-REFERENCE TO RELATED APPLICATIONS

This application is a Continuation-in-Part (CIP) of U.S. patent application Ser. No. 12/146,471, filed on Jun. 26, 2008, and entitled "RECOGNIZING GESTURES FROM FOREARM EMG SIGNALS."

BACKGROUND

1. Technical Field

A "Wearable Electromyography-Based Controller" provides a physical device, worn by or otherwise attached to a user, that directly senses and decodes electrical signals produced by human muscular activity using surface Electromyography (sEMG) sensors. The resulting electrical signals provide a muscle-computer interface for use in controlling or interacting with one or more computing devices or other devices coupled to a computing device.

2. Related Art

In general, as is well known to those skilled in the art, Electromyography (EMG) measures the muscle electrical activity during muscle contractions as an electrical potential between a ground electrode and a sensor electrode. EMG can measure signals either directly within the muscle (invasive EMG) or on the skin above a muscle (surface EMG).

Invasive EMG is very accurate in sensing muscle activation, but is generally considered to be impractical for human-computer interaction applications as it requires needle electrodes to be inserted through the skin and directly into the muscle fibers. In contrast, surface EMG, while less accurate, only requires that conductive sensors be placed on the surface of the skin. Surface EMG is fundamentally noisier than invasive EMG since motor unit action potentials (MUAPs) must pass though body tissues such as fat and skin before they can be captured by a sensor on the surface. Due to the high sensitivity of EMG sensors required to detect these signals, they also typically detect other electrical phenomena such as activity from other muscles, skin movement over muscles, and environmental noise, etc.

The EMG signal is an electrical potential, or voltage, changing over time. The raw signal is an oscillating wave with an amplitude increase during muscle activation. Most of the power of this signal is contained in the frequency range of 5 to 250 Hz. A typical statistic computed over the raw EMG signal for diagnosis of muscle activity is the windowed root mean squared (RMS) amplitude of the measured potential. This RMS measure of EMG signals has typically been employed for diagnostic purposes such as evaluating muscle function during rehabilitation after a surgery or for measuring muscle activation to assess gait. RMS amplitude is a rough metric for how active a muscle is at a given point in time. Consequently, since most EMG-based applications have originated and are used in medical and/or clinical settings, certain assumptions are generally made about preparation and setup of EMG measurement devices, and about the measurement and processing of EMG signals.

For example, since the medical utility of attaining the best possible signal is high, there is typically no perceived need to reduce the cost of preparation and setup at the cost of signal accuracy. Specifically, in setting up EMG devices in a clinical setting, the skin is typically first cleaned with an abrasive so that dead skin cells are removed. EMG sensors are then typically carefully placed by an expert, who can locate the exact locations of muscle bellies and find the optimal placement. Further, in some cases, a current is then applied through the sensors to test sensor placement accuracy. For example, if the electrode is placed on a muscle that is expected to control a particular finger and a current is applied to the muscle via the electrode in the EMG sensor, the expected finger should twitch, if not, then sensor would be relocated to the correct position.

Further, since EMG sensors are generally carefully placed in clinical settings, they are usually treated as being static (i.e., mapped directly to specific muscles of interest). Consequently, clinicians tend to place many constraints on users/patients in these scenarios. For example, the users/patients may not be allowed to move their bodies in certain ways (e.g., rotating the arm, since this would move the surface sensors away from the muscles of interest).

Human-computer interfaces (HCI) have been primarily implemented by monitoring direct manipulation of devices such as mice, keyboards, pens, dials, touch sensitive surfaces, etc. However, as computing and digital information becomes integrated into everyday environments, situations arise where it may be inconvenient or difficult to use hands to directly manipulate an input device. For example, a driver attempting to query a vehicle navigation system might find it helpful to be able to do so without removing his or her hands from the steering wheel. Further, a person in a meeting may wish to unobtrusively and perhaps invisibly interact with a computing device. Unfortunately, the general assumptions described above with respect to the setup and use of conventional EMG sensors and signal measurement tend to make the use and setup of conventional EMG systems impractical for typical HCI purposes which allow a user to control and interact with computing systems, applications, and attached devices.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A "Wearable Electromyography-Based Controller" as described herein, provides a hardware device or devices, implemented in various form factors, which is either worn by the user or temporarily attached to the user's body. In combination with associated initialization and configuration software and user interface techniques, the Wearable Electromyography-Based Controller provides a human computer interface (HCI) device that allows the user to control and interact with computing systems and attached devices via electrical signals generated by the movement of the user's muscles following initial automated self-calibration and positional localization processes. In other words, the Wearable Electromyography-Based Controller provides a user wearable muscle-computer interface (muCI).

In general, the Wearable Electromyography-Based Controller includes one or more integrated Electromyography (EMG) sensor nodes. The EMG sensor nodes within the Wearable Electromyography-Based Controller measure muscle electrical activity for use in muscle-computer interaction applications. However, unlike conventional Electromyography (EMG) measurement systems, the Wearable Electromyography-Based Controller described herein requires only general positional placement on the user's body. In fact, this general placement of the Wearable Electromyography-Based Controller is enabled by including more EMG sensors than are expected to be necessary to measure muscle electrical activity. An automated positional localization process is then used to automatically identify and select a subset of some or all of the sensor nodes that are in an appropriate position to collect muscle electrical signals corresponding to particular user gestures or movements.

More specifically, because various embodiments of the Wearable Electromyography-Based Controller includes an excess of EMG sensors, the initial positional localization process allows the overall system to self-select a set of one or more appropriate sensor nodes within the Wearable Electromyography-Based Controller in order to capture appropriate muscle electrical signals for controlling and interacting with computing systems and attached devices.

As noted above, the Wearable Electromyography-Based Controller can be implemented in various forms, including wearable devices or articles of clothing. For example, the Wearable Electromyography-Based Controller can be implemented as an armband, a wristwatch, eyeglasses (with sensors integrated into the frame), a shirt, gloves, or other article of clothing worn by the user, or any other physical device or collection of devices worn by the user. Further, it should also be understood that a user can wear multiple Wearable Electromyography-Based Controllers, with each such Wearable Electromyography-Based Controller being used to interact with either the same or a different computing device or application.

In view of the above summary, it is clear that the Wearable Electromyography-Based Controller described herein provides a unique device for measuring user muscle electrical activity for interacting with and controlling one or more computing devices following an initial positional localization process for self-selecting a set of appropriate EMG sensor nodes to capture the electrical activity associated with particular user gestures or motions. In addition to the just described benefits, other advantages of the Wearable Electromyography-Based Controller will become apparent from the detailed description that follows hereinafter when taken in conjunction with the accompanying drawing figures.

DESCRIPTION OF THE DRAWINGS

The specific features, aspects, and advantages of the claimed subject matter will become better understood with regard to the following description, appended claims, and accompanying drawings where:

DETAILED DESCRIPTION OF THE EMBODIMENTS

In the following description of the embodiments of the claimed subject matter, reference is made to the accompanying drawings, which form a part hereof, and in which is shown by way of illustration specific embodiments in which the claimed subject matter may be practiced. It should be understood that other embodiments may be utilized and structural changes may be made without departing from the scope of the presently claimed subject matter.

1.0 Introduction:

In general, a "Wearable Electromyography-Based Controller," as described herein, provides various techniques for measuring user muscle electrical activity to interact with and control one or more computing devices. More specifically, the Wearable Electromyography-Based Controller provides a wearable device having a set of electromyography (EMG) sensor nodes for detecting a user's muscle-generated electrical signals for interacting with and/or controlling general purpose computing devices, applications running on such computing devices, personal music players, physical devices coupled to a computing device (such as, for example, a pan-tilt-zoom camera, home automation system, musical instrument, etc.), game consoles, televisions or other multimedia devices, virtual devices such as a virtual piano or virtual guitar implemented within a computing environment, etc. Similarly, the Wearable Electromyography-Based Controller can be used to provide control of electromechanical prosthetic devices such as prosthetic hands, arms, legs, etc., by performing particular motions or gestures which in turn cause specific muscles of the user to generate electrical signals that are then used to activate one or more pre-determined motions in the prosthetic device.

The Wearable Electromyography-Based Controller is implemented in various form factors, including sets of individual sensor nodes (wired or wireless), wearable devices including a plurality of sensor nodes, or articles of clothing including a plurality of sensor nodes. For example, in various embodiments, the Wearable Electromyography-Based Controller is implemented as an armband, a wristwatch, eyeglasses, an article of clothing worn by the user (such as a shirt, gloves, shoes, pants, headband, etc.), or any other physical device or collection of devices worn by the user that has sufficient contact with the surface of the user's skin to the user to measure the electrical activity one or more of the user's muscles. Further, it should also be understood that a user can wear multiple Wearable Electromyography-Based Controllers, with each such Wearable Electromyography-Based Controller being used to interact with either the same or a different computing device, application, or other attached device.

Figure 2:
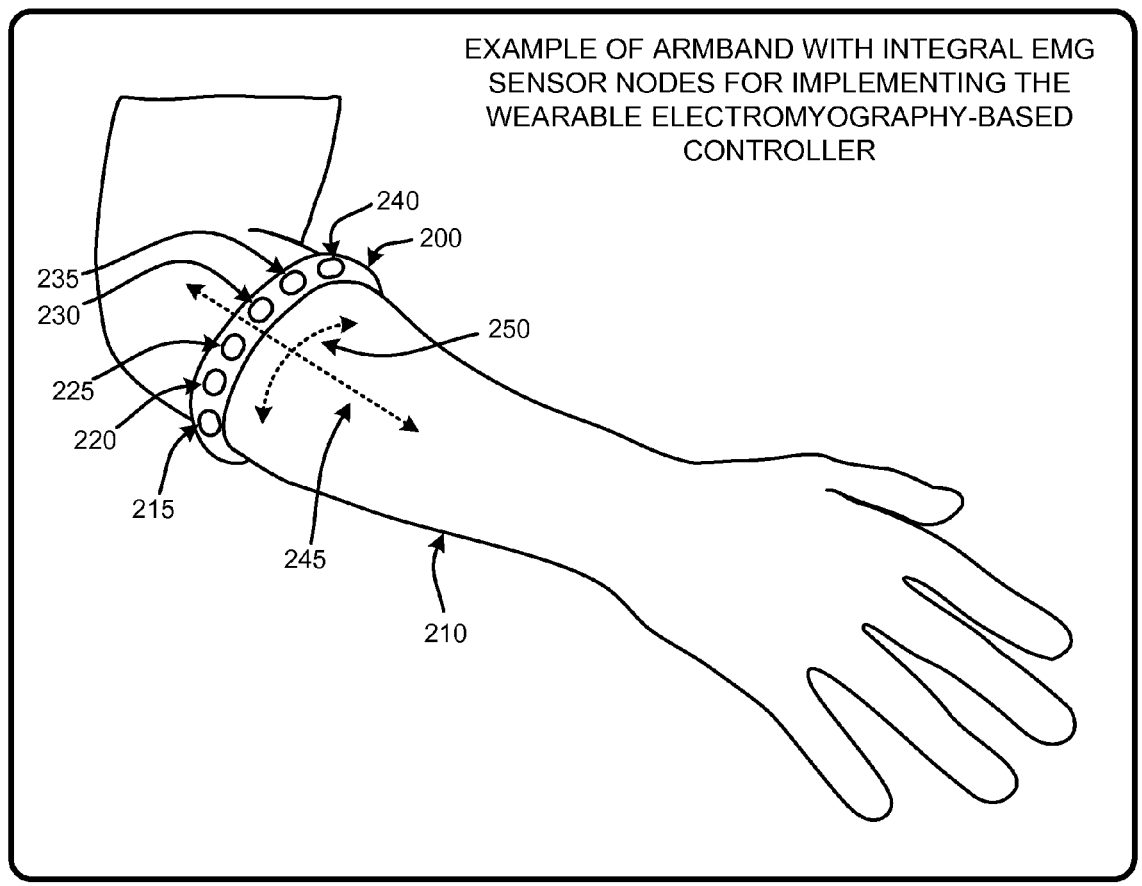
FIG. 2 provides an example of a wireless embodiment of the Wearable Electromyography-Based Controller implemented in the form of an armband, as described herein.

For example, in one embodiment, the EMG sensor nodes of the Wearable Electromyography-Based Controller are placed in a simple band which is worn around the users forearm in order to sense muscle activity associated with specific finger and hand gestures (see discussion of FIG. 2 for an example of this embodiment). One example of this embodiment is described in a co-pending U.S. patent application entitled "RECOGNIZING GESTURES FROM FOREARM EMG SIGNALS," filed Jun. 26, 2008, and assigned Ser. No. 12/146,471, the subject matter of which is incorporated herein by this reference. This co-pending patent application generally describes an initial process for learning muscle electrical signals corresponding to particular user gestures or motions for use in allowing the Wearable Electromyography-Based Controller to provide the desired human computer interface (HCI), also referred to herein as a muscle-computer interface (muCI).

In contrast to conventional Electromyography (EMG) measurement systems, the Wearable Electromyography-Based Controller described herein requires only general positional placement on the user's body. In fact, this general placement of the Wearable Electromyography-Based Controller is enabled by including more EMG sensors than are expected to be necessary to measure muscle electrical activity, with automated sensor selection being performed during an initial positional localization process. Consequently, the initial positional localization process allows the overall system to self-select a set of one or more appropriate sensors within the Wearable Electromyography-Based Controller in order to capture appropriate muscle electrical signals for controlling and interacting with computing systems and attached devices. Note that in various embodiments, the automated positional localization is repeated either periodically, or on as as-needed basis, in case the Wearable Electromyography-Based Controller moves relative to one or more particular muscles during use.

Further, in various embodiments, non-selected EMG sensors within the Wearable Electromyography-Based Controller are automatically turned off in order to save power. This embodiment is particularly useful in wireless implementations of the Wearable Electromyography-Based Controller where an onboard battery (replaceable or chargeable), fuel cell, photovoltaic power cell, etc., is used to energize selected EMG sensor nodes and associated circuitry. It should also be noted that in wireless implementations of the Wearable Electromyography-Based Controller, communication between the Wearable Electromyography-Based Controller and one or more computing systems is accomplished via conventional wireless communications protocols such as, for example, radio frequency (RF) communications, infrared (IR) based communications, Bluetooth, Zigbee, etc. In this case, the Wearable Electromyography-Based Controller includes one or more wireless transmitters, and optionally one or more receivers, for directly interfacing with one or more computing devices, or interfacing with one or more "hubs" that serve as intermediaries for interfacing the Wearable Electromyography-Based Controller with one or more computing devices.

It should be understood that various embodiments of the Wearable Electromyography-Based Controller are implemented in wired embodiments, such as, for example, by including an integrated USB cable or the like that both provides the necessary power for the EMG sensor nodes and provides a communications pathway between the Wearable Electromyography-Based Controller and one or more computing devices. As in the wireless case, in wired embodiments, the Wearable Electromyography-Based Controller communicates either directly with computing devices, or with those computing devices via an intermediary hub.

In addition, given the various wired and wireless embodiments of the Wearable Electromyography-Based Controller described above, it should be understood that hybrid embodiments using various elements of both the wired and wireless configurations are enabled. For example, in one embodiment, a power cable provides operational power, while wireless communications are then enabled by one or more transmitters/receivers integrated into, or coupled to, the Wearable Electromyography-Based Controller. For example, in these types of hybrid embodiments, the power cable (e.g., a power cable connected to a transformer or other power source, or a USB power cable connected to a computing device or transformer, etc.) provides operational power to the Wearable Electromyography-Based Controller, while the wireless transmitters/receivers provide communications between the Wearable Electromyography-Based Controller and one or more computing devices or intermediary hubs within wireless range of the Wearable Electromyography-Based Controller.

Some of the advantages offered by the Wearable Electromyography-Based Controller are that the Wearable Electromyography-Based Controller enables muscle electrical signal based HCI or muCI type control of computing devices, applications, and attached devices with little or no preparation and setup on the part of the user. In fact, in the simplest embodiment, the user simply generally places the Wearable Electromyography-Based Controller in an approximate position (e.g., forearm, wrist, legs, chest, shoulders, back, etc.) that requires little or no expertise or attention to specific sensor node placement. Further, the automated positional localization of the Wearable Electromyography-Based Controller allows users to move freely as they would if they were not wearing the device.

In addition, the use of multiple EMG sensor nodes in combination with one or more Wearable Electromyography-Based Controllers also allows various applications associated with the Wearable Electromyography-Based Controller to detect muscle strain and provide ergonomic feedback to the user. Consequently, in various embodiments, the Wearable Electromyography-Based Controller can be used for training a user to execute complex sets of specific muscular activities, such as required for playing musical instruments or sports, or for operating particular devices by providing immediate haptic, audio, or visual feedback to the user in response to specific motions or gestures by the user.

In view of the above summarized capabilities, and in further view of the following detailed description, it should be understood that the Wearable Electromyography-Based Controller provides users with a "universal" input mechanism that can be used to control any computing device, applications running of computing devices, electronic or mechanical devices coupled to a computing device, or any other electronic device (television, radio, appliance, light switch, etc.) having an appropriate infrastructure or interface for receiving input from a wired or wireless controller. Note also that the use of a small wearable device such as the Wearable Electromyography-Based Controller, which may be under the user's clothes, if desired, provides a mechanism that is unobtrusive (i.e., the user can be using her hands to perform other tasks while using Wearable Electromyography-Based Controller to provide active control of one or more devices). Further, it should also be appreciated that the control and interface capabilities provided by the Wearable Electromyography-Based Controller are potentially invisible in the sense that a user wearing one or more such controllers can remotely interact with various devices without anyone else being able to see or hear any overt actions by the user to indicate that the user is interacting with such devices.

1.1 System Overview:

As noted above, the "Wearable Electromyography-Based Controller" provides a unique device for measuring user muscle electrical activity for interacting with and controlling one or more computing devices following an automated positional localization process for self-selecting a set of appropriate EMG sensor nodes to capture the electrical activity associated with particular user gestures or motions. The processes summarized above are illustrated by the general system diagram of FIG. 1. In particular, the system diagram of FIG. 1 illustrates the interrelationships between functional modules for implementing various embodiments of the Wearable Electromyography-Based Controller, as described herein.

Figure 1:
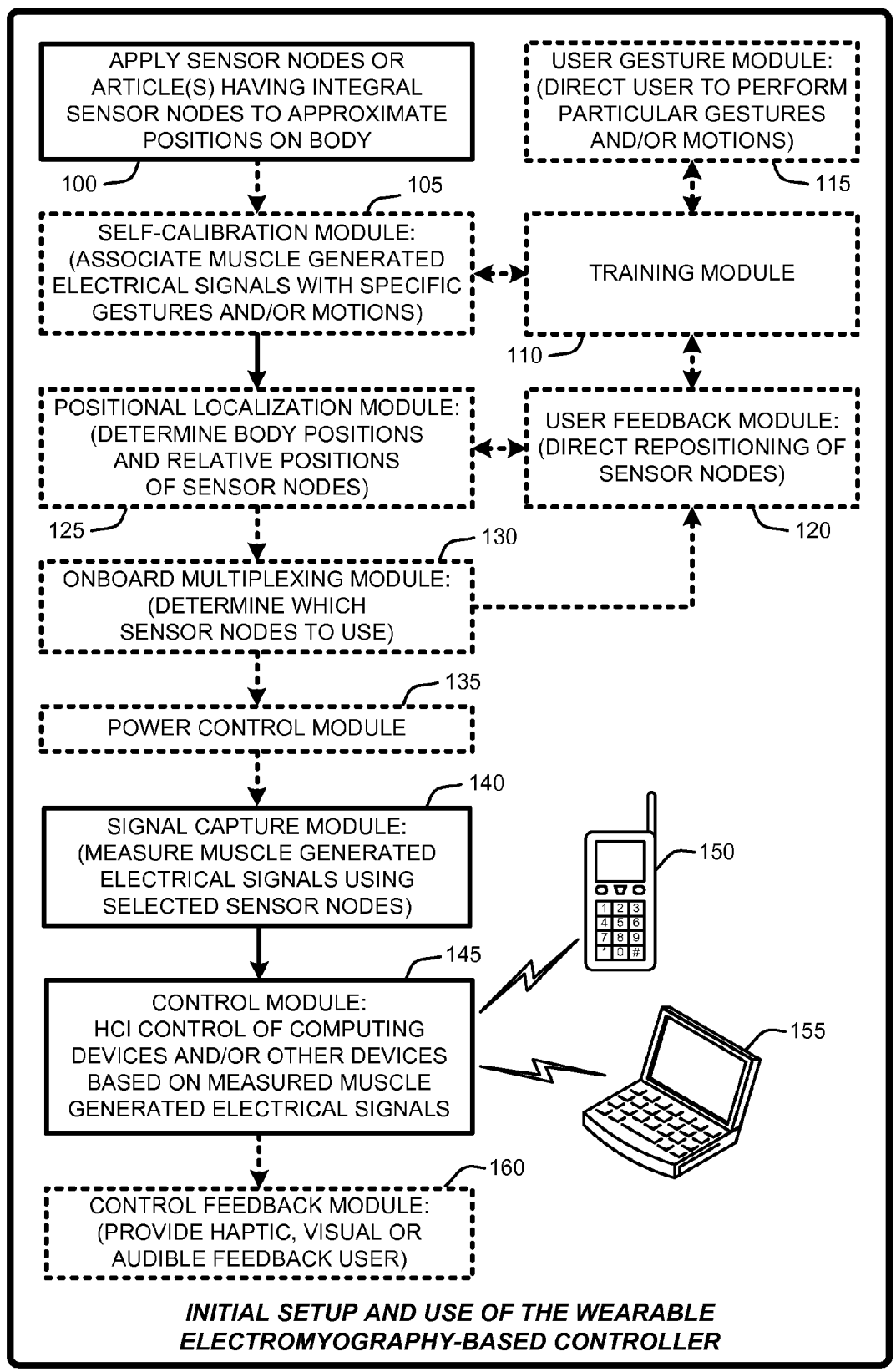
FIG. 1 provides an exemplary architectural flow diagram that illustrates program modules for implementing various embodiments of the Wearable Electromyography-Based Controller, as described herein.

Furthermore, while the system diagram of FIG. 1 illustrates a high-level view of various embodiments of the Wearable Electromyography-Based Controller, FIG. 1 is not intended to provide an exhaustive or complete illustration of every possible embodiment of the Wearable Electromyography-Based Controller as described throughout this document. In addition, it should be noted that any boxes and interconnections between boxes that may be represented by broken or dashed lines in FIG. 1 represent alternate embodiments of the Wearable Electromyography-Based Controller described herein, and that any or all of these alternate embodiments, as described below, may be used in combination with other embodiments that are described throughout this document.

In general, as illustrated by FIG. 1, the Wearable Electromyography-Based Controller operates by first applying 100 or otherwise attaching the sensor nodes of the Wearable Electromyography-Based Controller to one or more locations on the user's skin. As described in greater detail in Section 2.2, the sensor nodes are either provided as individual sensor nodes, or as a set or group of sensor nodes integrated into a wearable article or device, such as, for example, an armband, wristwatch, article of clothing, etc.

In various embodiments, once the user has initially attached the Wearable Electromyography-Based Controller, a self calibration module 105 operates in cooperation with a training module 110 to associate the electrical signals (or a particular sequence of electrical signals) generated by particular muscles with specific gestures or motions of the user. In some embodiments, a user gesture module 115 works in cooperation with the training module 110 by directing the user to perform specific gestures or motions to assist the training module 110 and self-calibration module in learning the muscle generated electrical signals or sequences of muscle generated electrical signals that correspond to the specific gestures and motions of the user. Further, in various embodiments, a user feedback module 120 operates to direct the user in repositioning or rotating the Wearable Electromyography-Based Controller in order to better position one or more of the sensor nodes to capture particular muscle electrical signals.

Note that this initial self-calibration and training process is described only generally herein, as the specifics of these processes are the subject of the aforementioned co-pending U.S. patent application Ser. No. 12/146,471, the subject matter of which is incorporated herein by this reference. However, it should be understood that in various embodiments, the initial calibration and training is repeated either periodically, or on an as needed basis (either automatically, or in response to specific user direction to repeat the calibration) to account for changes in measured muscle electrical activity as the result of movement of one or more of the sensor nodes during use. See Section 2.3 for an additional discussion of the initial self-calibration process.

Once the initial self-calibration process has been completed, a positional localization module 125 operates to determine approximate positions of each sensor node on the body, as well as relative positions of one or more of the sensor nodes relative to one or more other of the sensor nodes. In addition, during the positional localization process, in various embodiments, the aforementioned user feedback module 120 may again operate to direct the user in repositioning or rotating the Wearable Electromyography-Based Controller in order to better position one or more of the sensor nodes to capture particular muscle electrical signals. Note that the automated positional localization of the Wearable Electromyography-Based Controller is described in further detail in Section 2.4.

Following the positional localization process, the Wearable Electromyography-Based Controller is ready to use in order to capture electrical signals generated by the user's muscles and to then use those electrical signals to form the basis of a muscle-computer interface. However, in various embodiments, additional features of the Wearable Electromyography-Based Controller are implemented in order to improve the overall efficiency and utility of the Wearable Electromyography-Based Controller. For example, in one embodiment, a multiplexing module 130 is used to determine which sensor nodes should be used to capture the muscle generated electrical signals of particular muscles. Note that the multiplexing module 130 may also operate in cooperation with the user feedback module 120 to assist the user in properly positioning the Wearable Electromyography-Based Controller. See Section 2.5 for an additional discussion of sensor node multiplexing.

In a related embodiment, a power control module 135 is used to power down or disable one or more sensor nodes that are not being used (based on the determinations made by the multiplexing module 130). Such embodiments are particularly useful for wireless embodiments of the Wearable Electromyography-Based Controller that use an onboard power source that must be periodically recharged or replaced.

In either case, a signal capture module 140 then receives the muscle generated electrical signals captured by each active sensor node of the Wearable Electromyography-Based Controller. These electrical signals are then interpreted (based on the aforementioned self-calibration and training processes) by a control module 145 that interfaces with computing devices, or "hubs" acting as intermediaries between the Wearable Electromyography-Based Controller and one or more computing devices. The control module 145 then provides HCl (or muCl) for interacting with and controlling one or more computing devices, 150 and/or 155, or devices coupled to or otherwise controlled by such computing devices. Note that once the muscle-generated electrical signals have been interpreted, the control module 145 operates like any other HCl device, such as a keyboard, mouse, etc., to interface with various computing devices.

Finally, since the Wearable Electromyography-Based Controller operates based on muscle generated electrical signals, in various embodiments, a control feedback module 160 is used to provide feedback to the user to let the user know that a particular command has been entered or executed by the user. For example, in the case of a keyboard, the user will know when she has pressed a particular key. Similarly, in the case of a mouse, the user will know when he has clicked one of the mouse buttons, or used the mouse to move a cursor on a display device. However, in the case of Wearable Electromyography-Based Controller, it may not be immediately apparent to the user that a command has been successfully entered or executed by the user.

Therefore in various embodiments, the control feedback module 160 of the Wearable Electromyography-Based Controller operates to provide haptic, visual, or audible feedback to the user to inform the user that a command has been successfully entered or executed in response to muscle generated electrical signals resulting from gestures or motions of the user.

Examples of haptic feedback include a vibrating device in the Wearable Electromyography-Based Controller (not shown in FIG. 1) that provides a tactile indication to the user that a command has been successfully entered or executed. Similarly, one or more of the sensor nodes of the Wearable Electromyography-Based Controller can be used to apply an electrical stimulation to the skin of the user, thereby causing one or more muscles to react.

In the case of visible feedback, examples include integrating one or more lights into the Wearable Electromyography-Based Controller. In this case the lights (e.g., a ring of LED lights around the exterior of an armband implementation of the Wearable Electromyography-Based Controller) will light up, either all at once, or in some predefined sequence or pattern to inform the user that a particular command has been successfully entered or executed. Similarly, a display device, either coupled to the Wearable Electromyography-Based Controller (e.g., a small OLED display or the like), or coupled to a computing device being controlled by the Wearable Electromyography-Based Controller can also provide visual feedback to the user. For example, in the case that the Wearable Electromyography-Based Controller is being used to move a cursor and to select one or more elements on the screen, the user will have immediate visual feedback simply because the user will be watching the cursor and directing the selection of particular elements while using the Wearable Electromyography-Based Controller for HCI purposes.

Finally, examples of audible feedback include playing a tone, sound clip, music, speech, or other audio output when a command has been successfully entered or executed.

Note also that haptic, visual, and/or audible feedback may also be used to provide negative feedback to indicate that a command was not successfully entered or executed in response to a particular gesture or motion by the user.

2.0 Operation of the Wearable Electromyography-Based Controller:

The above-described functional modules and components are employed for implementing various embodiments of the Wearable Electromyography-Based Controller. As summarized above, the Wearable Electromyography-Based Controller provides a unique device for measuring user muscle electrical activity for interacting with and controlling one or more computing devices following an initial positional localization process for self-selecting a set of appropriate EMG sensor nodes to capture the electrical activity associated with particular user gestures or motions.

The following sections provide a detailed discussion of the operation of various embodiments of the Wearable Electromyography-Based Controller, and of exemplary methods for implementing the functional modules and components described in Section 1 with respect to FIG. 1. In particular, the following sections examples and operational details of various embodiments of the Wearable Electromyography-Based Controller, including: sensing muscle electrical activity using EMG sensors; wearable devices with EMG sensor nodes; initial self-calibration; positional localization of EMG electrodes and/or sensor nodes; on-board multiplexing for determining which individual sensors or sensor nodes to enable or disable; automated feedback regarding placement and setup of EMG sensors and/or sensor nodes; haptic feedback mechanisms; determination of when to engage or disengage active control using the Wearable Electromyography-Based Controller; and additional embodiments and considerations.

2.1 Sensing Muscle Electrical Activity with EMG:

In general, human skeletal muscles are made up of muscle fibers attached to bone by tendons. These muscles contract to create skeletal movement. To contract a muscle, the brain sends an electrical signal through the nervous system to motor neurons. These motor neurons then transmit electrical impulses known as action potentials to the adjoining muscle fibers, causing the muscle fibers to contract. The combination of a motor neuron and the attached muscle fibers are known as a motor unit. Each muscle is made up of many motor units. During muscle contraction, some subset of a muscle's motor units is activated. The sum of all the electrical activity in a motor unit during contraction is generally referred to as a motor unit action potential (MUAP).

The MUAP or electrical signals produced by the body during muscle contractions is typically measured with electromyography (EMG). An EMG sensor can measure muscular electrical signals from the surface of the skin. While easy to apply, a surface EMG sensor can produce a somewhat noisy signal as the muscular electrical signals must pass though body tissues such as fat and skin before they can be captured at the surface of the skin. Due to the sensitivity of EMG sensors required to detect these signals, they also typically detect other electrical phenomena such as activity from other muscles, skin movement over muscles, and environmental phenomena. The Wearable Electromyography-Based Controller provides various techniques for capturing the electrical signals produced by muscle movement and using those signals to provide a muscle electrical signal based HCI, as described in detail herein.

2.2 Wearable Devices with EMG Sensor Nodes:

As discussed above, the Wearable Electromyography-Based Controller may be implemented in a number of form factors. For example, in one embodiment, as illustrated by FIG. 2, the Wearable Electromyography-Based Controller is implemented as a wearable armband 200 that is worn on the user's forearm 210. In general, the armband 200 has a plurality of EMG sensor nodes (215, 220, 225, 230, 235 and 240) around the circumference of the armband. In general, when implemented as an armband 200 or the like, the Wearable Electromyography-Based Controller will have an elastic consistency such that the EMG sensors (215, 220, 225, 230, 235 and 240) contained within the armband will firmly contact the skin of the forearm 210 when the band 200 is worn.

In the example of the Wearable Electromyography-Based Controller illustrated by FIG. 2, a wired or wireless interface (not shown) is used to communicate with a computing device that processes the signals generated by the sensors (215, 220, 225, 230, 235 and 240). Any conventional means of communication, RF, IR, wired connections, etc., may be used. Note that due to the aforementioned self-calibration and positional localization processes performed to prepare the Wearable Electromyography-Based Controller for use, there is no requirement that the EMG sensor nodes (215, 220, 225, 230, 235 and 240) be uniformly spaced.

In fact, these self-calibration and positional localization processes allow the Wearable Electromyography-Based Controller (such as the armband 200) to be somewhat arbitrarily placed on the arm 210. For example, as indicated by the double sided arrows having broken lines (245 and 250) illustrated in FIG. 2, the armband 200 can be placed in varying orientations and locations on the forearm, by moving the armband up or down the arm or rotating the armband to position one or more of the sensor nodes in particular positions.

Once the armband has been placed, as muscles contract in the forearm, the EMG sensor nodes (215, 220, 225, 230, 235 and 240) will detect the corresponding electrical activity and transmit the signals. The armband 200 may transmit raw signals or it may have a processor to perform some initial signal processing, for example rectification, noise reduction, filtering, etc. In yet another embodiment, the armband 200 may be provided with sufficient processor and storage capacity to perform the computational tasks described below, in which case the armband 100 recognizes particular user gestures or motions and transmits signals indicating that particular actions corresponding to those gestures of motions are to be performed.

Other wearable device configurations may also be used. For example, the Wearable Electromyography-Based Controller can be implemented as an armband (as illustrated by FIG. 2), a wristwatch, an article of clothing worn by the user such as a snug fitting shirt, or any other physical device or collection of devices worn by the user that is sufficient to ensure that one or more sets of sensor nodes are in contact with approximate positions on the user's skin.

Figure 3:
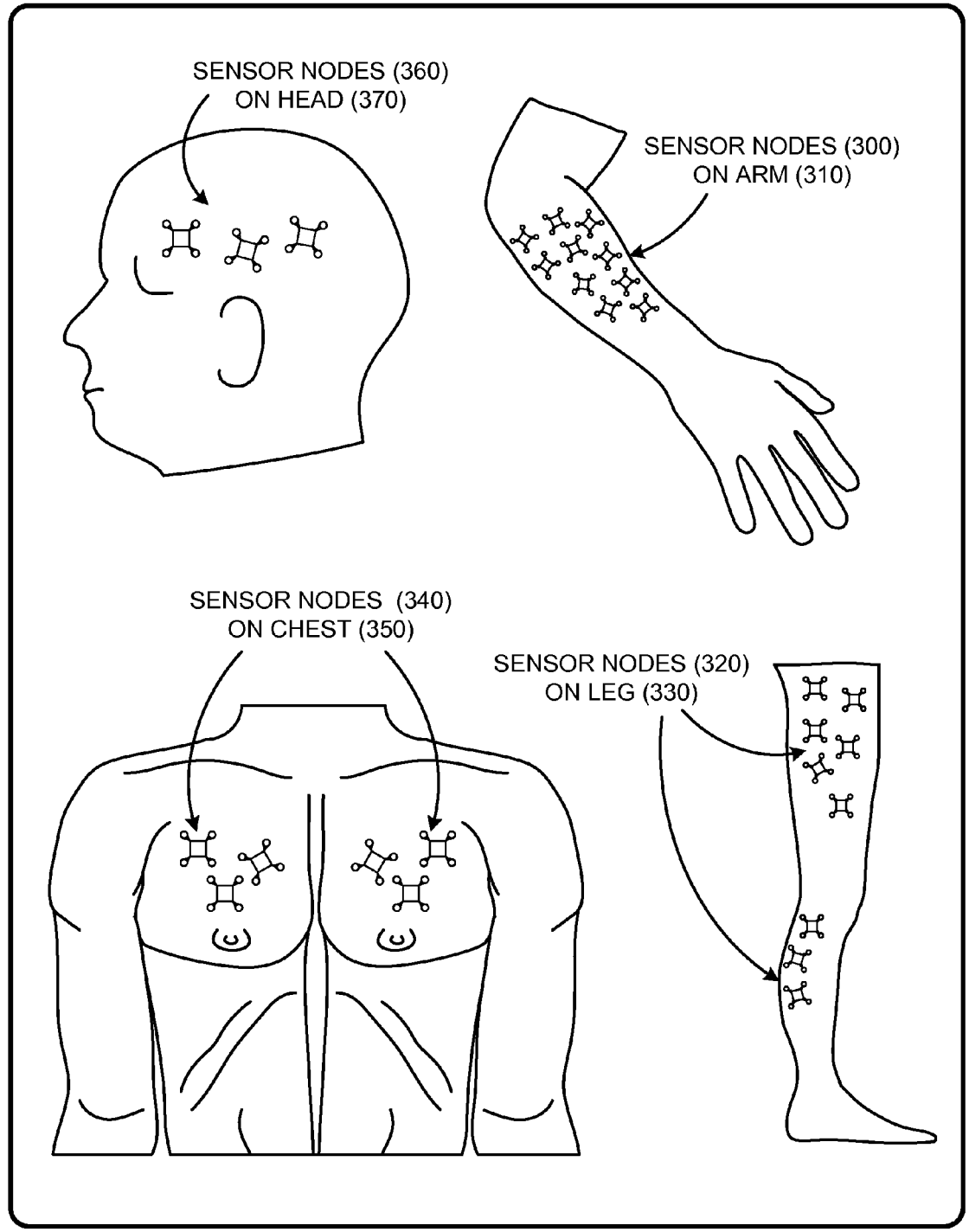
FIG. 3 illustrates individual EMG-based sensor nodes coupled to various parts of the user's body for implementing various embodiments of the Wearable Electromyography-Based Controller, as described herein.

It should also be noted that the techniques described herein can also be used with one or more sets of individual EMG sensor nodes, such that a wearable device is not necessary. In this case, the individual EMG sensor nodes may be placed on various positions on the user's body without regard for precise location of muscle bellies. General examples of such embodiments are illustrated by FIG. 3 which shows sets of individual sensor nodes 300, 320, 340 or 360, placed in various positions on various parts of the user's body, including the user's arm, leg, chest and head, 310, 330, 350 and 370, respectively.

Note that in general, individual sensor nodes are either wireless, in the sense that they can communicate wirelessly (RF, IR, etc.) with one or more computing devices or "hubs" as discussed in further detail below, or are wired such that they are coupled to a computing device or hub in order to provide the desired HCI. Similarly, where multiple sensors are integrated into a wearable device such as an armband, wristwatch, or an article of clothing, for example, those sensors may be coupled to one or more wireless transmitters contained within or coupled to the wearable device such that the overall Wearable Electromyography-Based Controller is wireless in the sense that it provides wireless HCI capabilities to the user based on electrical signals generated by the user's muscles. However, in various embodiments, each of the individual sensor nodes included in a device such as the armband described above with respect to FIG. 2, may include its own wireless communications capability as with individual sensor nodes such as those shown in FIG. 3.

In addition, in the case that multiple sensors are integrated into a wearable device, in various embodiments, the wearable device includes fewer amplifiers than individual EMG sensors. Such embodiments are useful for several reasons. For example, as discussed in further detail in Section 2.5, onboard multiplexing is used in various embodiments to determine which sensor nodes are to be used, and which are to be ignored. In this case, the active sensor nodes (i.e., the nodes determined to be useful for capturing particular muscle generated electrical signals) are assigned to one of the available amplifiers (e.g., using digital or analog multiplexing or switching). Further advantages of this embodiment include both size and cost reductions for embodiments of the Wearable Electromyography-Based Controller which include integrated EMG sensor nodes, since conventional amplifiers tend to be both larger and more expensive than the electrodes of the EMG sensors. Consequently, large numbers of EMG electrodes can be used in combination with relatively few amplifiers by multiplexing a subset of the EMG sensor electrodes to the available amplifiers to provide acceptable coverage of particular muscles.

Figure 4:
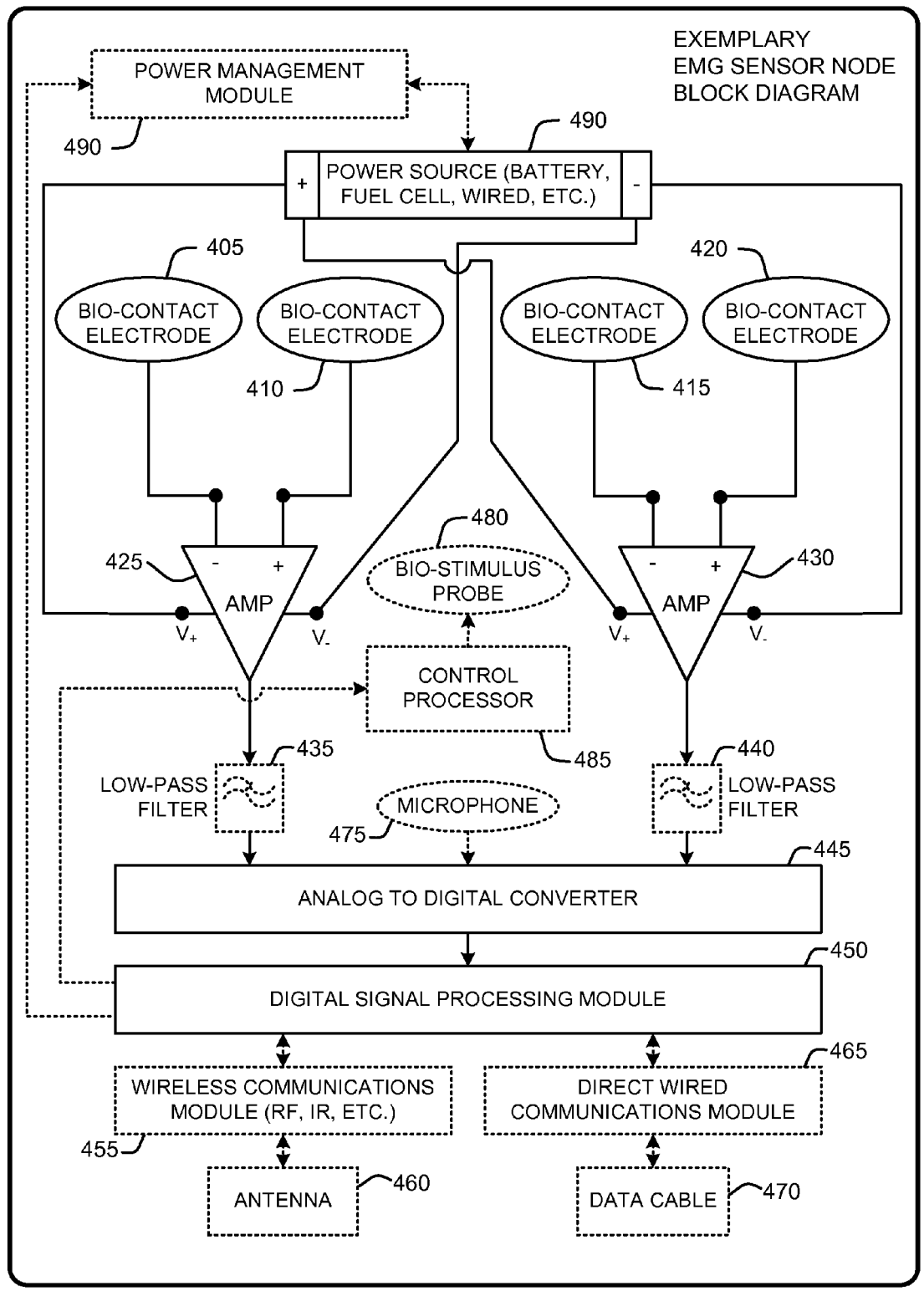
FIG. 4 illustrates an exemplary block diagram showing general functional units of individual EMG-based sensor nodes for implementing various embodiments of the Wearable Electromyography-Based Controller, as described herein.

2.2.1 Example EMG Sensors and Sensor Nodes:

As noted above, EMG sensor nodes may be either wired or wireless, and may be implemented either with amplifiers, or without amplifiers in the case of multiplexing. FIG. 4 provides an exemplary block diagram of a sensor node for implementing various embodiments of the Wearable Electromyography-Based Controller.

For example, as illustrated by FIG. 4, in various embodiments, each sensor node contains two pairs of bio-contact electrodes (also referred to herein as "probes"), e.g., electrode pair 405 and 410, and electrode pair 415 and 420, that are intended to be in contact with the user's skin. Note that while each sensor node can include only a single electrode pair, the use of two (or more) pairs of electrodes in each sensor node has been observed to aid in determining proper placement and data collection from the EMG electrodes (or probes), as discussed in further detail in Section 2.4.1.

Each pair of electrodes (405/410 and 415/420) is connected to an amplifier 425 or 430 (either directly, or via multiplexing as described in Section 2.5). Electrical signals collected by each pair of each pair of electrodes (405/410 and 415/420) is therefore amplified and optionally low-pass filtered via optional low pass filters 435, 440. In general, the purpose of the low-pass filters 435 and 440, is to eliminate or attenuate high frequency noise captured by the pairs of electrodes (405/410 and 415/420).

Captured electrical signals, whether or not filtered are then passed to an onboard A/D converter 445 that generates a digital signal from the amplified muscle electrical signals. A digital signal processing (DSP) module 450 evaluates the digital signal and sends a corresponding signal or command to the computing device or hub (not shown). Note that transmission of the signal or command received from the DSP module is either wireless or wired. In the case of wireless transmission, a wireless communications module 455 is integrated with or coupled to the sensor node in combination with a small antenna 460 to provide the necessary wireless communications. In the case of wired transmission, a direct wired communications module 465 is integrated with or coupled to the sensor node in combination with a data cable 470 to provide the necessary communications path between the sensor node and the computing device or hub.

In various embodiments, one or more of the sensor nodes also includes an integral microphone 475. As discussed in detail in Section 2.4.3, in various embodiments, sound-based positional localization is used to assist in determine approximate and relative positions of the various sensor nodes once attached to the surface of the user's skin. In general, sound signals captured by the microphone are passed to the A/D converter 445 and eventually transmitted to the computing device or hub using wireless or wired communications as described above.

In addition, in various embodiments, one or more of the sensor nodes also includes a bio-stimulus probe 480 which provides another pair of electrodes for applying an electrical signal to the skin of the user under the direction of a control processor 485. In general, the control processor 485 generates electrical stimulus signals in response to direction received from the DSP module 450, which in turn receives commands to generate electrical stimulus signals via the wireless or direct wired communications modules 455 and 465, respectively.

As discussed in further detail in Section 2.4.1, the electrodes of EMG sensors are usually used for sensing electrical potentials, but can also apply them to the skin. When one sensor node is applying a potential to the skin, the other sensor nodes are "listening" to see how strong that potential is when it reaches them (far-away electrodes will not see this potential at all). Using the relative strength of applied potentials at other sensor nodes, the system determines which electrodes are near each other and can build an approximate "map" of sensor locations for use in biopotential-based positional localization. Note that while a separate pair of electrodes comprising the bio-stimulus probe 480 is illustrated in FIG. 4 for purposes of explanation, it should be clear that either or both the bio-contact electrode pairs (405/410 and 415/420) can be used to apply a potential to the skin by suitable connecting those electrode pairs to the aforementioned control module 485.

Finally, each sensor node needs a power source 490 to operate. In various embodiments, the power source 490 is integrated into the sensor node, such as by using a battery, fuel cell, photovoltaic power cell, etc. In related embodiments, the power source 490 is provided via a direct power connection from an external power source. Note also that in the case that multiple sensor nodes are integrated into a device such as an armband, wristwatch, or article of clothing, the "external" power source can be integrated into that device. For example, in the case of an armband type Wearable Electromyography-Based Controller, one or more onboard batteries can be included in the armband itself to apply power to the sensor nodes contained in that armband. In addition, as noted above, and as discussed in further detail in Section 2.5 with respect to onboard multiplexing, in various embodiments, unneeded sensor nodes (or individual electrode pairs) are selectively enabled or disabled via a power management nodule 495 in order to conserve power. Such embodiments are especially valuable in the case where the onboard power source 490 is limited.

2.3 Initial Self-Calibration:

In general, it is assumed that users of the Wearable Electromyography-Based Controller will not place the device (or individual sensor nodes) in exactly the same place or orientation relative to specific muscles each time that the user wears the Wearable Electromyography-Based Controller. Consequently, one of the advantages of the Wearable Electromyography-Based Controller is the capability to rapidly self-calibrate each time that it is placed into position or otherwise activated.

Calibration can be accomplished in various ways. For example, in one embodiment, calibration is accomplished by training or retraining a classification system with gestures of interest every time the device is worn. This particular technique is described in the aforementioned co-pending U.S. patent application entitled "RECOGNIZING GESTURES FROM FOREARM EMG SIGNALS," filed Jun. 26, 2008, and assigned Ser. No. 12/146,471.

In general, this co-pending patent application describes a process wherein the user is directed to make specific hand and finger motions following initial placement of the Wearable Electromyography-Based Controller. The resulting muscle-generated electrical signals captured by the various EMG sensor nodes of the Wearable Electromyography-Based Controller are then evaluated and used to train a classification system which then uses some or all of the EMG sensor nodes of the Wearable Electromyography-Based Controller to recognize specific hand and finger movements of the user, with those movements then being used to provide the desired HCI. As discussed above, in various embodiments, the user may be directed to move or rotate the position of the Wearable Electromyography-Based Controller during the calibration process in the case where the measured muscle generated electrical activity is insufficient to properly train or calibrate the classification system to accurately discriminate between particular user movements.

Note that in training or retraining the classification system, as described in the described in the aforementioned co-pending patent application, the user is generally directed to perform all gestures or movements forming a set of movements that can be differentiated by the classification system. However, given the limited number of muscles involved in such gestures, in various embodiments, the classification system is trained or calibrated by using only a subset of recognized gestures or motions in order to find matching points from previously built models.

For example, as described in the aforementioned co-pending patent application, if the user has used the Wearable Electromyography-Based Controller before and has trained models for predicting her gestures, she can simply perform a clenching gesture, or a wriggling of his fingers (in the case of an armband) in order to provide the system with enough information to perform the mapping from the current position of EMG sensors (and of data) to the previous model. Further, in various embodiments, this calibration is continually or periodically performed as the system observes the user's actions. Note that periodically or continuously performing the calibration serves at least two purposes. First, repeating the calibration process may help to further refine the gesture model, and second, repeating the calibration process will help to adjust for minor positional movements of the Wearable Electromyography-Based Controller on the user's body.

In addition, since the Wearable Electromyography-Based Controller is worn by the user, calibration data can be collected even when the user is not actively engaged in using the Wearable Electromyography-Based Controller for HCI purposes. This additional calibration data collection allows the system to statistically model likely gestures or movements, and given enough time, the system can infer the gestures or movements that the user is performing.

Further, in various embodiments, the user is provided with various mechanisms for performing user-defined gestures or sequences of gestures, and then assigning particular actions to those gestures, either from a pre-defined list of actions, or from user defined actions or macros. In this case, the training described above is the same, with the difference simply being the particular command or macro that is being mapped to the predefined or user-defined gesture.

2.4 Positional Localization of EMG Electrodes or Sensor Nodes:

In traditional EMG environments, an expert finds a specific muscle and carefully places electrodes relative to that muscle, then manually tells any downstream computer or logging system which muscle each sensor has been placed on. However, in contrast to the manual system requiring expert placement, the Wearable Electromyography-Based Controller does not require an expert to carefully label the position of each sensor, and in fact, the Wearable Electromyography-Based Controller does not require that sensor locations be the same from one session to another, or even that sensors do not move during a particular session in which the Wearable Electromyography-Based Controller is being used to provide user control and interaction with computing systems and attached devices via electrical signals generated by the movement of the user's muscles.

In various embodiments of the Wearable Electromyography-Based Controller, EMG sensors (also referred to herein as "sensor nodes"), and associated electronics (including amplifiers, electrodes, power sources, etc., as described in further detail in Section 2.2.1 with respect to FIG. 4), either integrated into a wearable article, such as an armband or other article, or in the form of individual sensors, can be placed at various approximate locations around the body. For example, as illustrated by FIG. 3, a user might wear sets of one or more sensors 300 on each arm 310 in combination with one or more sets of one or more sensors 320 on each leg 330. Other possible locations for sensors 340 may include the chest 350, or sensors 360 on the head 370, or any other desired area or combination of areas of the body.

In order to accurately decode the electrical potentials read by the electrodes of each sensor node into gestures or commands that can be used to interact with and control applications or devices coupled to or controlled by various computing devices, it is helpful to know approximately where on the body each specific sensor is, and which sensors are in relatively close proximity to other sensors. Further, knowing the approximate and relative positions of the various sensors allows the Wearable Electromyography-Based Controller to perform a number of additional functions in various embodiments.

For example, as discussed in further detail in Section 2.5, positional information enables various power management embodiments where particular sensors are automatically turned off or powered down (i.e., enable or disabled) to save energy (or onboard power) in the case that the particular sensors either provide information that is not relevant or is redundant with respect to one or more other sensors. For example, if a particular application only cares about arm movements to provide the desired HCI, sensors on other parts of the body can be disabled or ignored. Further, if an application only cares about coarse arm movements, and two arm sensors are sufficiently close to each other, one of those two sensors can be disabled, since enabling both of them may capture unnecessarily redundant muscle electrical signals for use in interacting with the particular application.

Positional localization is also important since accurate decoding of muscle generated electrical signals generally depends on knowing approximate sensor locations on the body. For example, if the decoding system has a model that depends on knowing the level of activation in the biceps muscle, it is important to know exactly which sensors are, in fact, reading signals from the biceps muscle. Similarly, if two sensors have signals that look similar, the overall system needs to know if that is because two different muscles are being activated together, or just because these two electrodes happen to be right next to each other.

As noted above, automated setup of the Wearable Electromyography-Based Controller depends on automatically figuring out where the various sensors are physically located on the user's body. In various embodiments, as described in further detail in Sections 2.4.1 through 2.4.3, there are several different techniques, which can be used either separately or in combination to automatically determine the placement and relative location of individual sensors or nodes. In each case, these localization processes involve coordinating multiple nodes using a "hub" or a sensor node that has sufficient onboard computing power to perform the positional localization operations described below.

Note that the "hub" can be a computing device in communication with the Wearable Electromyography-Based Controller, or can be integrated into the Wearable Electromyography-Based Controller itself. An example of a case where the hub is integrated into the Wearable Electromyography-Based Controller is a wristwatch where the watch contains some computational capability and the watch band includes a plurality of integral sensors. Note that such a wristwatch would measure electrical activity of the muscles of the wrist or forearm using a plurality of EMG sensors. Further, in various embodiments, such a wristwatch would then communicate with one or more other computing devices to provide the desired HCI.

As described herein, communication between the Wearable Electromyography-Based Controller and computing devices or hubs is either wireless (e.g., RF, IR, etc.), or wired via a data cable or the like coupled to the Wearable Electromyography-Based Controller. However, for purposes of explanation, the more complex wireless embodiment will be described in the following sections, with the understanding that all wired embodiments will also be enabled by simply replacing the wireless communications capability of the Wearable Electromyography-Based Controller with a wired connection (as described above with respect to FIG. 4) to the computing device or hub.

2.4.1 Biopotential-Based Positional Localization:

In various embodiments, during initial positional localization, individual sensor nodes (including the sensor nodes integrated into devices such as armbands, wristwatches, etc.) "take turns" applying electrical potentials to the surface of the skin. In other words, each sensor node takes a turn acting as a "source stimulator" to apply an electrical potential to the skin that is then read by the other sensor nodes. It should be understood that electrodes of EMG sensors are usually used for sensing potentials, but can also apply them to the skin. When one sensor is applying a potential to the skin, the other sensors are "listening" to see how strong that potential is when it reaches them (far-away electrodes will not see this potential at all). Using the relative strength of applied potentials at other sensor nodes, the positional localization system (residing on a hub or remote computer in the case that the Wearable Electromyography-Based Controller does not have sufficient onboard computing power to perform this task), determines which electrodes are near each other and builds an approximate "map" of sensor locations.

Figure 5:
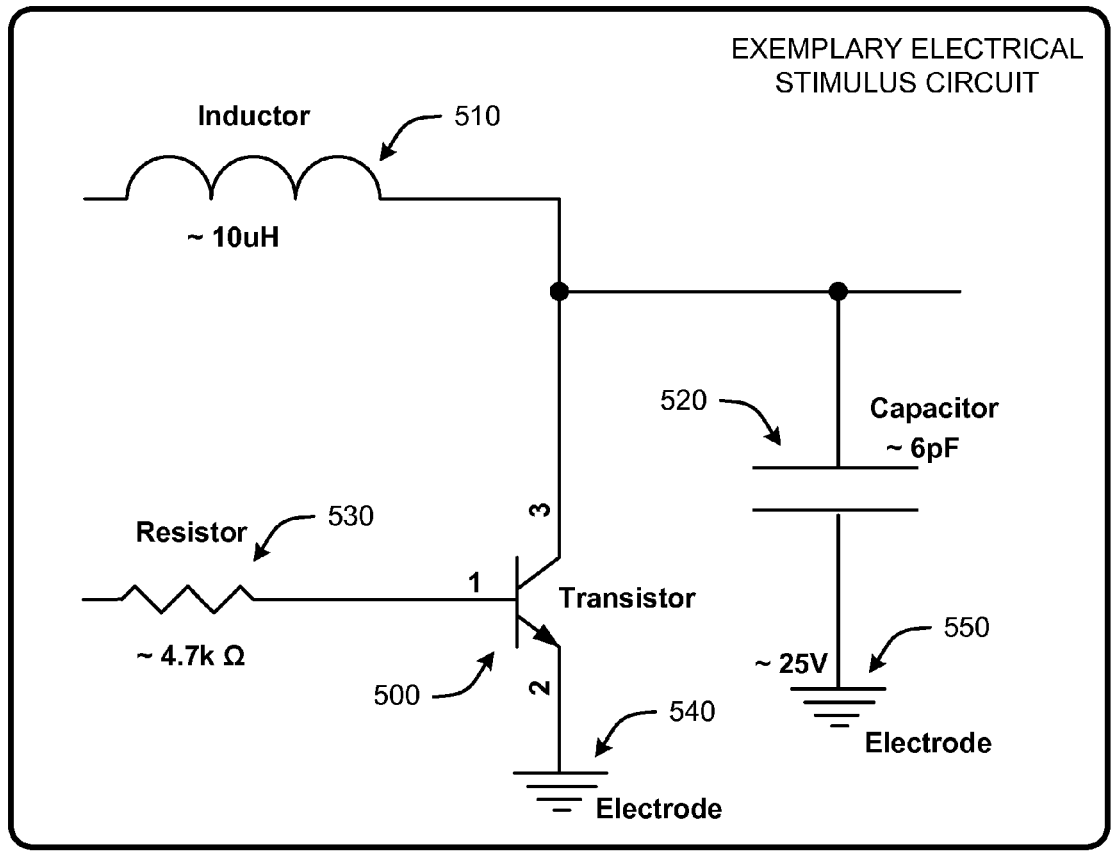
FIG. 5 illustrates an exemplary electrical stimulus circuit as a component of the EMG-based sensor node, for implementing various embodiments of the Wearable Electromyography-Based Controller, as described herein.

During electrical stimulation and sensing, the hub or other computing device again controls all the calibration and data extraction via the wired or wireless link to each sensor node. Each bio-stimulus probe has two electrodes that touch the skin. The separation between these electrodes is relatively small (on the order of about 16 mm in a tested embodiment); however separation can vary depending upon the level of electrical potential being applied to the skin. In a tested embodiment, the electrical stimulus was generated using a switched LC circuit as shown in FIG. 5. It should be understood that there are numerous ways in which an electrical stimulus waveform or signal can be generated, and that the circuit illustrated by FIG. 5 is intended to show only one such technique for generating a stimulus signal.

In general, the electrical stimulus circuit of FIG. 5 is a basic LC circuit that includes a transistor 500 which conducts current through an inductor 510 until steady state is reached and then quickly turns off. The energy in the inductor 510 then causes a capacitor 520 to charge and then a damped oscillatory condition continues for a few cycles. This switching is repeated in a manner to re-energize the circuit when the damped wave is on the order of about 10% of its initial values.

This process is then repeated for a fixed time $T_{ON}$ and then is discontinued. After waiting a fixed time $T_{OFF}$ the switching again causes a set of ringing. The combination of the inductor 510, capacitor 520 and resistor 530, in combination with a power source (not shown) controls the amount of electrical potential generated across electrodes 540 and 550. In the example shown, the LC circuit of FIG. 5 will apply a potential to the user's skin on the order of about 25V (with sufficiently low current that it is either unnoticeable or not uncomfortable to the user).

Figure 6:
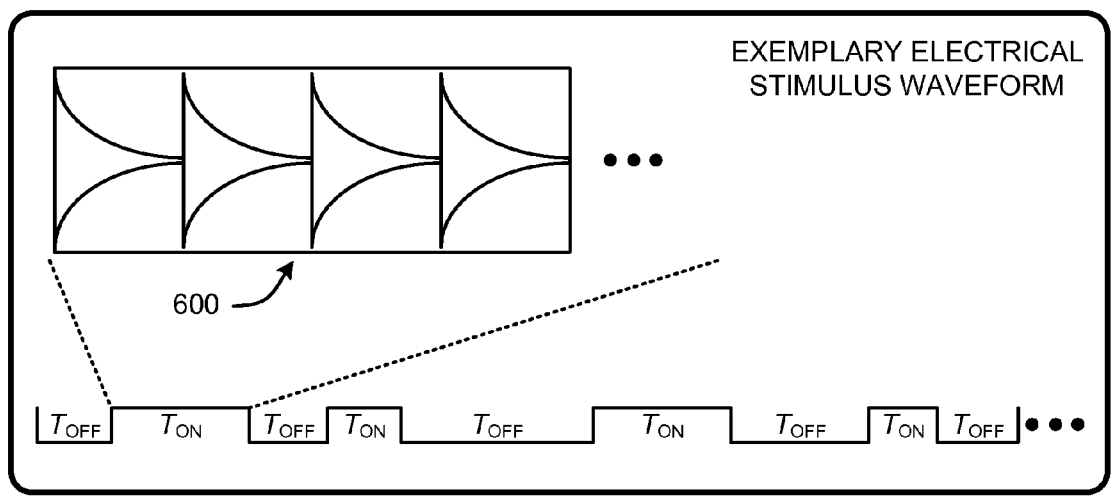
FIG. 6 illustrates an exemplary electrical stimulus waveform generated by the electrical stimulus circuit of FIG. 5, for implementing various embodiments of the Wearable Electromyography-Based Controller, as described herein.

FIG. 6 shows a typical wave form 600 generated by the electrical stimulus circuit of FIG. 5. Note that the $T_{ON}$ and $T_{OFF}$ periods form a pseudorandom sequence with strong autocorrelation. $T_{ON}$ is set to allow analog to digital converters and filters of all sensor nodes to measure the electrical potential in their region. The high frequency of the LC circuit helps to stimulate the skin even when the contacts are not optimally positioned. This stimulus also allows detection of the proper application of the probes on each sensor node being used as a source stimulator. In particular, since each sensor node has two pairs of probes or electrodes, if either of the probe pairs on that sensor node are significantly different than the other, or if the two sets do not follow mean and deviation of probes of other source stimulators, then the hub can distinguish a poorly placed probe and alert the user or discredit the data collected from that probe.

Note that the Wearable Electromyography-Based Controller is expected to operate in a generally noisy environment which includes other electrical phenomena such as activity from other muscles, skin movement over muscles, environmental noise, etc. Consequently, the use of the aforementioned pseudorandom sequence with autocorrelation makes it significantly easier to detect the resulting electrical stimulus signals in the midst of high levels of noise, and to determine the signal strength above the noise level.

2.4.2 RF-Based Positional Localization:

In various embodiments, positional localization is accomplished using RF transmission based localization techniques. For example, similar to the biopotential-based processes described in Section 2.4.1, individual sensor nodes "take turns" broadcasting known wireless signals (see discussion of Wireless communications module and antenna with respect to FIG. 4). When one sensor is broadcasting, the other sensors are "listening" to see how strong that wireless signal is when it reaches them. Using the relative strength of radio signals at other sensor nodes, the positional localization system determines which electrodes are near each other and builds an approximate "map" of sensor locations.

More specifically, during positional localization using RF, each sensor node is commanded to be an RF transmitter (i.e., a "transmitter node") for a given time while all of the other nodes are monitoring radio "receive signal" strength and link quality data. Then, the transmitter node stops and a time-slotted communication between each node and the hub allows the hub to collect data from the particular RF transmission source. Next, a different sensor node becomes the transmitter node and the process described above is repeated until all nodes have acted as the transmitter node. The hub then builds a matrix of nearest neighbors by comparing RF signals quality measured among the various source transmissions. Although the frequency of the nodes is high to allow for compact antennas (e.g., 2.45 GHz in a tested embodiment of the Wearable Electromyography-Based Controller), the relative position of many of the nodes is still in the near field of the measurement source.

In various embodiments of the Wearable Electromyography-Based Controller, loop antennas are used for each wireless sensor node. Note that for loop antennas, the near field is mainly magnetic field coupling. Further, with loop antennas, the rotation of the source transmission around its normal does not affect the near field magnetic field. The transmissions from the source are in a series of on or off times providing a maximal length pseudorandom code to allow strong autocorrelation but weak cross correlation with noise and interference.

Figure 7:
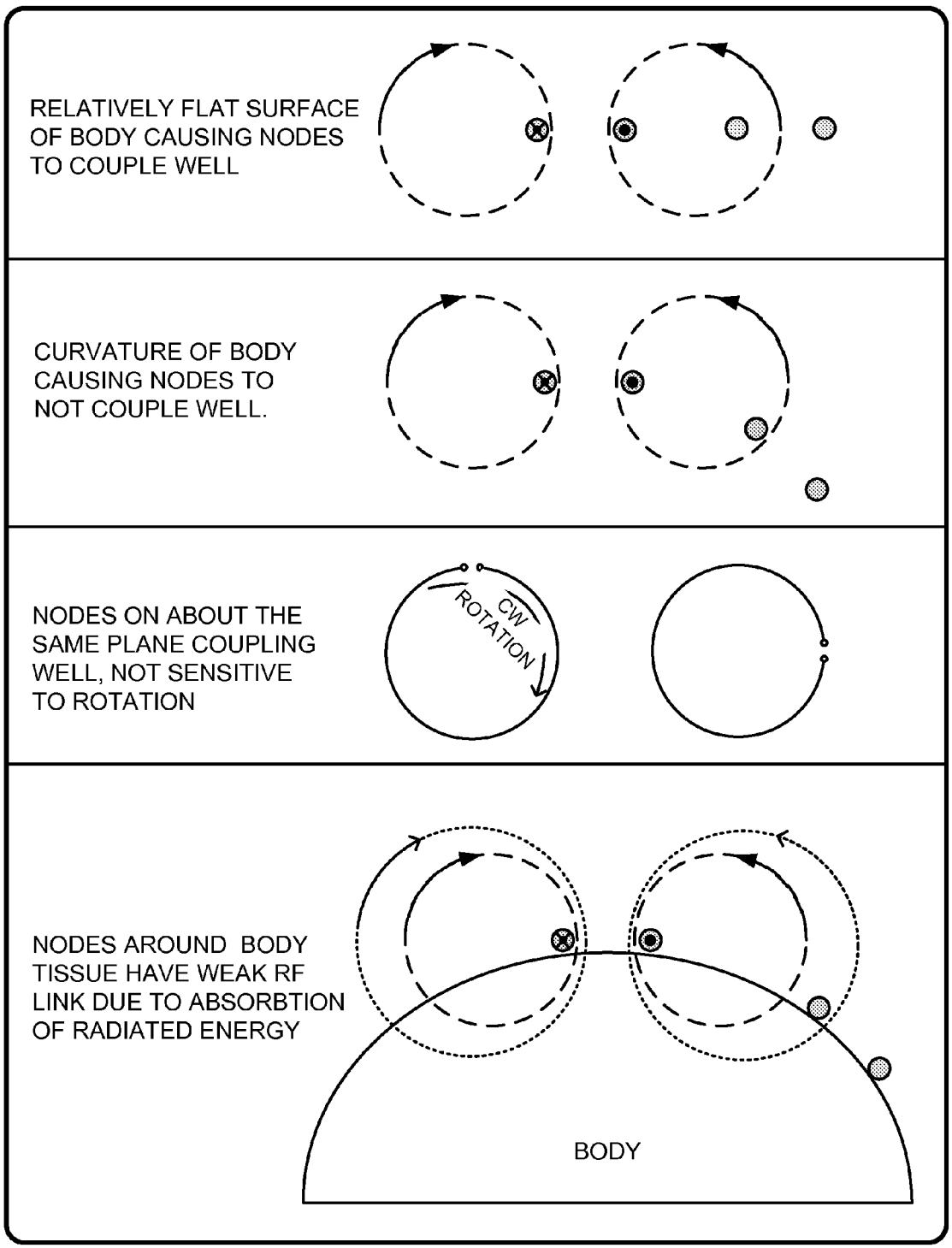
FIG. 7 illustrates the effect of placing sensor nodes in different relative positions on the user's body with respect to the use of radio-frequency (RF) based positional localization of sensor nodes, as described herein.

Another advantage when using closely spaced sensor nodes is that the nearest neighbor nodes tend to be in the same plane as the transmitter. For near field this means better magnetic field coupling. As the normal to the loop antenna rotates with respect to the source transmitter, the coupling decreases and so node on parts of the body that are farther away or on strongly curved areas show weaker coupling. Also near neighbors in the same plane as the source transmitter are insensitive to rotation around their own normal. This allows indication of near neighbor center spacing rather than center and rotational position. Also the RF signal is absorbed by body tissue so as the nodes separated by body the signal strength drops rapidly. FIG. 7 provides several illustrations showing the source transmitter and a near neighbor with coupling and rotation effects based on the relative position of sensor nodes on the user's body when the wireless sensor nodes use loop antennas.

2.4.3 Sound-Based Positional Localization:

In addition to positional localization based on either or both biopotentials or RF transmission and reception, positional localization can also be based either in part, or entirely, on the use of sound sources for positional localization (see discussion of FIG. 4 for an example of sensor nodes having integral microphones. Note that microphones may also serve as small speakers, thereby allowing such sensor nodes to act as a "sonic source node".

For example, similar to the biopotential-based and RF-based positional localization processes described in Sections 2.4.1 and 2.4.2, respectively, 2.4.2, individual sensor nodes "take turns" as the "sonic source node" broadcasting a known sound pattern at a known frequency. Then, when one sensor is broadcasting a sound signal, the other sensor nodes are "listening" to see how strong that sound signal is when it reaches them. Using the relative strength of sound signals received by the microphones of the other sensor nodes and the precise time taken to transmit audio signals from one node to another (e.g., "time of flight", which can be accurately measured for sound), the positional localization system determines which electrodes are near each other and builds an approximate "map" of sensor locations.

In general, during sound stimulation and sensing for sound-based positional localization, the hub again controls all the calibration and data extraction via the aforementioned wireless or wired link. For this calibration an external sound source is needed. This external sound source can be implemented in various ways, such as, for example, by using the microphone of each sensor node as a speaker, by coupling or integrating one or more separate speakers or transducers to a wearable device such as the aforementioned armband, wristwatch or article of clothing having integrated sensor nodes, or by using one or more user positioned external sound sources. Sound sources such as approximately flat transducers on the order of about 5 to 10 mm diameter have been observed to provide good sound-based positional localization results.

More specifically, the surface acoustic wave generated by a speaker or transducer will travel through the skin and be exponentially attenuated as it enters muscle tissue. Consequently, sound travel through skin is preferred because it helps distinguish spatial position of sensor nodes on the surface of the skin. In various embodiments, a mixture of tones (such as dual tone, for example) is used to help avoid interference from other potential sound sources including environmental noise that might otherwise interfere with positional localization efforts based on sound transmission and receipt.

Because the Wearable Electromyography-Based Controller is intended to be used by individual users without requiring expert placement of individual sensor nodes, sound source positions are easily positioned by the user, and are not required to be located with extreme accuracy. In fact, so long as the sound source is in an approximately close position relative to the sensor nodes which are in turn approximately located with respect to a particular body part (e.g., armband on the user's forearm), acceptable sound-based positional localization results can be achieved.

In general, all sensor nodes listen when the sound source is at each of one or more different positions. The tones are made in bursts in a pseudorandom sequence with strong autocorrelation. As discussed above with respect to biopotential-based positional localization, the use of a pseudorandom sequence with autocorrelation makes it significantly easier to detect the resulting sound signals in the midst of high levels of noise, and to determine the signal strength above the noise level. Microphones in each sensor node then measure the level of the tones received by the microphone. The computing device or hub then uses the varying sound levels captured by each of the different sensor nodes to determine relative positions of each sensor node to each other sensor node, and to determine the position of each sensor node relative to the absolute position of the sound source placement.

Figure 8:
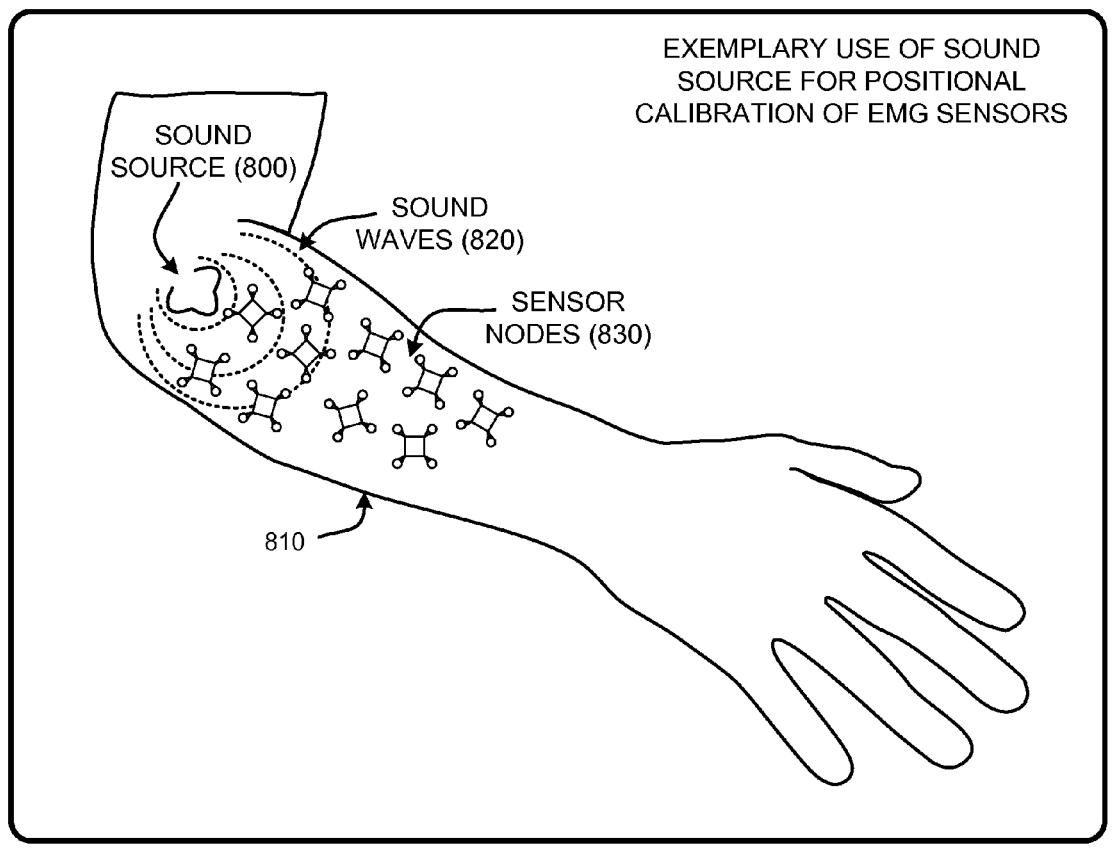
FIG. 8 illustrates the use of a sound source for providing positional localization of sensor nodes, as described herein.

FIG. 8 shows an example of using a separate sound source 800 on the surface of the user's forearm 810. As illustrated by FIG. 8, sound waves 820 (illustrated as curved broken lines) radiate out from the sound source 800, and impinge on various sensor nodes 830 which then report the level of the measured sound to the hub (see discussion of microphones in sensor nodes with respect to FIG. 4). Note that as discussed above, while FIG. 8 illustrates the use of a separate sound source 800 placed by the user, the sound source may be implemented by using individual microphones in each sensor node 830 as a speaker device, or by integrating one or more speakers or sound transducers into the Wearable Electromyography-Based Controller (such as, for example an armband, wristwatch, glove, article of clothing, etc.).

2.5 On-Board Multiplexing:

As described above, when using the Wearable Electromyography-Based Controller large numbers of individual electrodes (EMG sensors) or sensor nods integrated into a wearable device can be placed at various locations on the arm or on other positions around the body. In either case, the total number of electrodes placed in any particular region of the user's body may be significantly more than what is needed for a particular application, and may be significantly more than the Wearable Electromyography-Based Controller can power and/or transmit information about, especially in wireless embodiments where onboard power usage is a concern. Consequently, in various embodiments, an on-board multiplexing process is user to determine which sensor nodes should be enabled or active, and which sensor nodes should be disabled or inactive.

In particular, because individual users rather than experts familiar with EMG sensor placement will be placing the Wearable Electromyography-Based Controller in position, the overall system benefits from "blanketing" particular regions of the user's skin with EMG sensors, and then deciding in software (e.g., on-board multiplexing) which electrodes are actually important. For example, in the aforementioned "armband" configuration, the armband might contain 64 sensor nodes (with each node having one or more electrode pairs or individual sensors), when a total of 10 or less sensors would be sufficient to measure the electrical activity of muscles in the user's forearm corresponding to particular hand and finger gestures. In this case, the multiplexing system (see discussion of the "multiplexing module" illustrated in FIG. 1) will go through an initial calibration phase to choose 10 of those sensors to enable. Signals collected from those sensors would then be amplified, processed, and transmitted, as described above; all other sensors or sensor nodes are either ignored or disabled entirely.

Clearly, given sufficient bandwidth and power, it may be useful to amplify and transmit all signals from all sensors and sensor nodes, then let the hub or downstream computing system choose which signals are important. However, for real-world devices having where power and bandwidth are generally at a premium, "multiplexing" allows the selection of a relevant set of individual sensors from a potentially large number of sensor nodes, before wireless transmission. This approach can be used to avoid wasting power and bandwidth on signals that are redundant, electrodes that are not making good contact with the skin, etc.

Note that the decision about which sensors to enable generally requires a fairly sophisticated analysis of the electrical signals captured by individual sensor nodes. In some embodiments, such analysis generally requires more computing power (and thus more electrical power) than would be integrated into the Wearable Electromyography-Based Controller or into individual sensor nodes. While such computing power and electrical power sources can be integrated into the Wearable Electromyography-Based Controller in various embodiments, this would tend to increase both the size and cost of the Wearable Electromyography-Based Controller. Consequently, in various embodiments, the multiplexing analysis is instead performed by a downstream hub or computing device.

For example, in one embodiment, the overall system will go through a brief high-power calibration phase where all signals are transmitted to a receiver (for example, a downstream PC-type computer or other computing device. The receiver then analyzes the signals and determines which wireless nodes are sufficient to provide the necessary information in order to interpret the muscle-generated electrical signals of the user with sufficient accuracy to provide the desired HCI. In various embodiments, this information is then passed back to the Wearable Electromyography-Based Controller which disables all individual sensors or entire sensor nodes that are not required for HCI purposes.

Note also, that in the event that the Wearable Electromyography-Based Controller moves, a particular sensor or sensor nodes fails to provide a good signal at some point, or it becomes necessary to measure the electrical signals generated by other muscles, the downstream receiver can at any time direct the Wearable Electromyography-Based Controller to enable or disable other individual sensors or entire sensor nodes. Similarly, in such cases, the downstream receiver can also direct that the initial high-power calibration phase is repeated to reselect the appropriate individual sensors or sensor nodes for amplification and transmission.

However, it should also be understood that the overall decision as to which sensors are "important" can be made using relatively simple logic that does not require significant computing power. In such cases, the Wearable Electromyography-Based Controller, or even individual sensor nodes, can have sufficient onboard computing capabilities and onboard power to locally decide whether or not to contribute their signals for HCI purposes. In this case, unnecessary signals are simply never transmitted to downstream processors.

In general, various embodiments of the Wearable Electromyography-Based Controller use one or more of three different techniques for deciding whether a particular signal is sufficiently important to transmit. As discussed in Sections 2.5.1, 2.5.2, and 2.5.3, these techniques include an evaluation of sensor or sensor node positional information, and available decoding power. In general, each of these techniques can be used either separately, or in any desired combination, for deciding which sensors are "important" to contribute to the broader concept of shutting down non-essential sensors or sensor nodes to allow rapid deployment of many sensors with minimal cost in terms of power and wireless bandwidth.

2.5.1 Multiplexing Based on Positional Information:

In Section 2.4, several mechanisms for obtaining positional information (the location of each electrode pair or sensor node) were described for the purpose of determining approximately where on the body each sensor or sensor node was positioned. This information can also be used for onboard multiplexing purposes. For example, if a particular application is only interested in arm movements, all sensors or sensor nodes not located on the arms can be automatically shut down or otherwise disabled. Alternatively, if two sensors (or entire sensor nodes) are determined, by one or more of the positional localization techniques described in Section 2.4, to be very close to each other, the overall system can automatically disable one of them since it will be assumed that they will provide redundant information. Note that physical proximity may not always be a sole determinant of signal value where individual muscles being monitored may be closer together, such as where the Wearable Electromyography-Based Controller is implemented in a glove that is worn on the hand.

2.5.2 Multiplexing Based on Raw Signal Analysis:

Some analyses can be performed on the raw sensor signals to determine which are likely to be "important", independent of any classification/gesture-recognition system. These analyses are generally computationally simple, and are thus suited to being performed on the microprocessors that are built in to each wireless sensor node or into an integrated device such as the aforementioned armband. However, as discussed above, such processing of raw signals can also be on a downstream receiver or processor during an initial high-power calibration phase. Examples of raw-signal analyses that can provide indications of signal relevance include measures of RMS amplitude or muscle-generated electrical signals and measured power bands.

For example, in the case of RMS amplitude, signals where measured voltages are very low are unlikely to be informative, and signals where measured voltages are unreasonably high are likely to represent poor connections or some external noise source. Signals within a known range of amplitude are most likely to be informative. In this case, a very simple logic test to determine whether a measured signal is within a simple range can be included in the individual sensor nodes, such as, for example, by adding a simple logic gate to the analog to digital converter or to the digital signal processing module described with respect to FIG. 4. Similarly, an analysis of individual frequency bands of measured signals can also be performed using very simple computational capabilities. For example, in the case that a particular signal where one or more individual frequency bands falls outside a "reasonable" or expected range in known frequency bands are unlikely to be informative.

2.5.3 Multiplexing as a Function of Available Decoding Power:

More complex evaluations of measured signals can address questions such as "which electrodes are actually helping the overall system to decode specific gestures or movements?" The multiplexing system can then selectively enable/disable electrodes accordingly. In general, this type of analysis will be performed on a downstream hub or computing device in the case that the computational capabilities of the individual sensor nodes or the Wearable Electromyography-Based Controller. However, given sufficient computing power within individual sensor nodes or the Wearable Electromyography-Based Controller, these analyses can be performed locally. Both such embodiments are clearly enabled in view of the discussions provided herein, and will generally be a factor of cost, where increasing the computational capabilities of the Wearable Electromyography-Based Controller or of individual sensor nodes is generally expected to increase the manufacturing cost and power requirements of such devices.

The basic approach to implementing this type a multiplexing process that decides which sensors contribute to the gestures or motions of interest can be implemented in various ways. For example, a simple example of such as approach is to ask the user to perform a known set of gestures (for example, "wiggle each finger in sequence" or "clap your hands, then take two steps forward"). This gesture pattern can be presented either verbally, textually, or visually as an animation or video on a computer screen or other display device. Similarly, the sequence can be a particular set of gestures or motions that the user learns once and then repeats each time the device is turned on.

In either case, the information from all electrodes is then presented to the machine learning system that will be used for gesture recognition (see discussion of initial self-calibration in Section 2.3). Generic metrics such as "information gain", or algorithm-specific metrics such as confidence, separability, etc., are then used to determine which sensors contribute the most to correctly classifying the known pattern of gestures being used for the initial self-calibration (or for repeating the self-calibration process either periodically or on an as needed basis as described above). The basic question being addressed by such metrics is "If electrode x is dropped from the gesture recognition analysis, how much worse would the decoding performance be?" The answer to this question is then used to identify a set or subset of sensors or sensor nodes to be enabled (or conversely, to be disabled) for use in accurately using the muscle-generated electrical signals of the user to provide the desired HCI.

2.6 Automated Feedback About Placement and Setup:

As discussed herein, EMG electrodes of the Wearable Electromyography-Based Controller are applied coarsely, without an expert present to ensure precise placement. For example, in the aforementioned armband configuration, an end-user can attach the armband in any rotational orientation, and/or at any position along the length of the arm, such that sensor electrodes are not precisely located over muscles. Therefore, in various embodiments, in order to allow rapid placement of electrodes by individual users while still ensuring adequate signal quality, automated feedback is provided the user to assist him in quickly adjusting the Wearable Electromyography-Based Controller (or individual sensor nodes) to ensure adequate signal strength and quality for gesture-based HCI purposes.

Given this approach, the basic process of "installing" the Wearable Electromyography-Based Controller can be implemented in a number of user-friendly ways. For example, initial positioning of the Wearable Electromyography-Based Controller can be accomplished using a process such as the simple three step process illustrated below:

1) The user puts the armband, ankle-band, wristwatch, or other Wearable Electromyography-Based Controller in a coarsely approximate location where the device is intended to be placed. For example, an armband would be coarsely placed somewhere on the users forearm. The system would then be activated or turned on (unless the system was already activated or turned on);
2) The user would then make coarse manipulations to the initial positioning of the device, such as, for example, rotating the armband, while receiving simple feedback about signal quality (such as a simple "meter" on a computer screen, a sound emanating from the device, or speech cues to direct the user with respect to specific motions);
3) Finally, the user would make fine adjustments to the position or orientation of the device (e.g., rotate and/or move the position of the Wearable Electromyography-Based Controller) until a simple goal is achieved, such as "meter goes above level 5," "sound stops", "vibration stops", etc.

In various embodiments, the feedback provided to the user during this simple adjustment process is visual (e.g., a bar or meter on a computer screen, on a portable music player, or on a small on-board LCD or series of one or more LEDs or lights), auditory (e.g., a noise that gets quieter as signal quality increases, or a voice saying "keep turning, keep turning, perfect!"), or haptic (e.g., the Wearable Electromyography-Based Controller vibrates or electrically stimulates one or more areas of the user's skin while the user should continue to adjust the device and stops vibrating or electrically stimulating the user's skin when the signal quality is adequate.

All of these feedback modalities require some measure of "how good" the placement of the system is at any given time. Therefore, in various embodiments, two general categories of metrics for determining signal quality during adjustment are provided. These general categories include raw signal analysis and decoding power, as described above with respect to multiplexing in Sections 2.5.2 and 2.5.3, respectively.

In general, as described above, these metrics are used to assist the overall system in determining which sensors or sensor nodes in a large set of sensors were sufficient for decoding the muscle-generated electrical signals of the user to accurately map those signals to particular gestures or motions. Consequently, these same metrics can be used to provide real-time feedback about placement of the Wearable Electromyography-Based Controller on the user's body. For example, the overall system can direct the user to rotate the armband until the RMS amplitude of all electrodes is maximized. Similarly, the overall system can direct the user to rotate his armband while wiggling his fingers, until the gesture-recognizer's confidence in decoding the gestures is maximized. Again, any of the visual, audible, or haptic techniques described herein can be used in directing the user to continue positioning the Wearable Electromyography-Based Controller (or individual sensor nodes).

2.7 Haptic Feedback for Eyes-Free, Mobile EMG Interaction:

As discussed above with respect to the use of a Wearable Electromyography-Based Controller implemented in the form of an armband, finger gestures are recognized through electrodes on the forearm in combination with a software-based decoding system (which can also be implemented in hardware, if desired). In traditional computer interfaces, constant feedback is given to the user about his interactions. Usually, this is visual feedback, such as the movement of a cursor on the screen, an animation of a button depressing while the mouse is clicking on it, a window animating down to the taskbar when the "minimize" button is clicked, etc. An analogous feedback system is also useful for a mobile, eyes-free input system such as the Wearable Electromyography-Based Controller described herein. However, by construct, visual feedback is not always available in many scenarios. Consequently, in various embodiments, alternative feedback mechanisms for acknowledging success (or failure) of EMG gesture recognition is provided. While not all human-computer interactions require feedback, there are a number of examples of interactions where some sort of feedback is generally anticipated or appreciated by the user.

For example, while people might wear a wireless EMG-based armband or other Wearable Electromyography-Based Controller continuously throughout their day, it is probable that they would likely not be constantly using it to interact with a computing device. This implies the need to be able to engage and disengage the associated gesture recognition system (i.e., turning the system on and off). When a user is turning the system on and off, whether through a predefined or user-defined gesture or series of gestures (e.g., a simultaneous two handed squeeze where the user has an armband on each arm), via a physical on/off type button or the like, via a verbal command (e.g., speech recognition), or through the use of other HCI devices or mechanisms, feedback indicating that the system is now on and ready to receive gestures or is off and not able to receive gestures is generally advantageous so that the user is aware of the current state of the Wearable Electromyography-Based Controller, and so that HCI commands are not inadvertently executed by the user.

Common to most user interfaces is the feedback that any command was recognized. For example, no matter where a user clicks on a screen with a mouse, he can feel the mouse button click and understands that even if he missed the intended target on the screen, he did click the mouse. Similarly, in a wireless EMG armband finger gesture recognition system, such as that described herein and in the aforementioned co-pending patent application, some type of feedback would be useful to indicate to the user that the system detected a gesture and the system is trying to decode that gesture.

In various embodiments, once a gesture has been recognized, the gesture recognition system informs the user of which gesture was recognized. This feedback will inform the user if the correct gesture was recognized, especially where a large repertoire of gestures is available, or whether the system made an error that the user needs to correct. This is analogous to the feedback a user receives visually when any command is initiated on a desktop computer. For example, during speech transcription, a user typically sees the recognized transcript and can stop to correct errors. Even more commonly, when the user uses a pointing device such as a mouse to "click" an application icon on the desktop, the user knows that he has performed the correct action because he sees the intended the application open.

Finally, in various embodiments, the gesture recognition system includes means for informing or otherwise indicating to the user that it attempted to decode a gesture, but it could not understand the gesture. This type of feedback prompts the user to repeat the gesture so the system can try again to recognize the gesture. This is analogous to visual or auditory error messages used by desktop PCs or other computing systems or devices. Note that repeated failures to recognize a particular gesture can be used as the basis for retraining or recalibrating the gesture recognition system to recognize a different set of input signals than previously expected for the particular gesture. See the discussion of initial self-calibration for the Wearable Electromyography-Based Controller in Section 2.3.

2.7.1 Examples of Feedback Mechanisms:

Traditional computer interfaces typically employ visual or auditory feedback to the user to keep the user informed. Visual or auditory feedback could similarly be used during setup and calibration of any of the various embodiments of the Wearable Electromyography-Based Controller. However, once the system is put into use in a mobile environment, other modes of feedback are generally more useful, since a user's auditory and visual channels may already be in engaged in some of the everyday activities that are supported by the Wearable Electromyography-Based Controller. Consequently, haptic feedback mechanisms, such as pressure and vibration on the surface of the skin underneath the armband (adjacent to the EMG electrodes) is a useful alternative to other feedback mechanisms that might otherwise distract the user from some activity which the user is currently engaged in.

There are a number of ways that haptic feedback can be presented to the user. For example, a binary state such as on/off can be indicated by the presence of a small amount of intermittent vibration or constant pressure. A ring (or multiple rings) of small vibrators around the armband can be used in conjunction to create the sensation of a motion to communicate complicated information such as which gesture was recognized.

For example, a vibration moving clockwise versus counterclockwise could indicate a left versus right gesture being recognized. Further, the speed at which the vibrations move around the ring could also indicate different types of feedback such as which gesture was recognized. These types of haptic feedback mechanisms are consistent with most or all of the various embodiments of the Wearable Electromyography-Based Controller described herein, including, for example, the armband-based form factor described with respect to FIG. 2.

Further, if Wearable Electromyography-Based Controller devices, such as armbands for example, are worn on both arms (or on other different areas of the body), the difference in feedback between the two arms (or other locations) can also indicate which gesture was recognized. For example, feedback about whether a left versus right gesture was recognized can be indicated by one armband vibrating faster or with larger amplitude. Clearly, it is not the specific haptic feedback examples discussed above, such as specific vibration or pressure patterns, that are important, but rather, what is important to understand is that the Wearable Electromyography-Based Controller provides the capability to supply haptic feedback to the user in any desired (or user defined) pattern or sequence.

2.8 Determination of When to Engage or Disengage Active Control:

One of the problems of a system that is always available and always recognizing user movements through muscle electrical signals is that system needs to be able to differentiate between normal everyday gestures performed not for interacting with the system (i.e., using the hands for everyday tasks) and explicit commands issued for the system to recognize. In conventional HCI literature, this problem is sometimes referred to "avoiding the Midas touch" where every user action is interpreted as an intentional command.

In order to avoid this problem, in various embodiments, the Wearable Electromyography-Based Controller uses gross movements that are robustly recognized, and are unlikely to be confused with everyday gestures, to engage and disengage the system, or to inform the system that a subsequent gesture will correspond to a command. With respect to the use of an armband-based Wearable Electromyography-Based Controller, examples of such movements include clenching the first hard, or a series of actions that are not likely to be performed normally, such as rotating the wrists outward, then inward, to the maximum point of comfortable rotation, or any other predefined or user-defined motion or gesture desired.

In related embodiments, voice recognition techniques are used to enable or disable active control based on muscle electrical signals captured by the Wearable Electromyography-Based Controller. For example, in one such embodiment, the user speaks a word or phrase (e.g., "enable controller device") to inform the system that subsequent user movements are to be used to provide active control based on measured muscle electrical activity. Similar verbal commands can be used to disengage active control using the Wearable Electromyography-Based Controller.

2.9 Additional Embodiments and Considerations:

As summarized in Section 1.1 with respect to FIG. 1, the Wearable Electromyography-Based Controller provides HCI capabilities based on electrical signals generated by the body in response to the contraction of one or more muscles. As such, it should be clear that the Wearable Electromyography-Based Controller is capable of being used for any of a number of purposes. For example, these purposes include interaction with conventional application such as interacting with a computer operating system by moving a cursor and directing simple object selection operations (similar to using a computer mouse to select an object), wired or wireless game controllers for interacting with game consoles or with video games operating on such consoles, control of pan-tilt-zoom cameras, interaction with home automation systems such as audio, video, or lighting controls, etc.

Other obvious uses for the Wearable Electromyography-Based Controller include local or remote control of robots or robotic devices, such as, for example, using a glove with embedded sensor nodes to control a remote robotic hand wielding tools or medical instruments. Other uses of such gloves operating as Wearable Electromyography-Based Controllers include a system for providing automated translation of American Sign Language into written or spoken English (or into any other desired language) in the case that the user has such a glove on one or both hands. Note also that the armband-based Wearable Electromyography-Based Controllers described herein can provide similar functionality following proper initial self-calibration, as described in Section 2.3. Similarly, the user can wear a sufficient number of Wearable Electromyography-Based Controllers to map the motions or gestures of multiple body parts (hands, arms, legs, head, etc.). Then, those motions are replicated in a physical robot or digital avatar that is either local or remote, with that replication occurring either in real-time or as a recorded series of events.

3.0 Exemplary Operating Environments:

The Wearable Electromyography-Based Controller described herein is operational for interfacing with, controlling, or otherwise interacting with numerous types of general purpose or special purpose computing system environments or configurations, or with devices attached or coupled to such computing devices.

Figure 9:
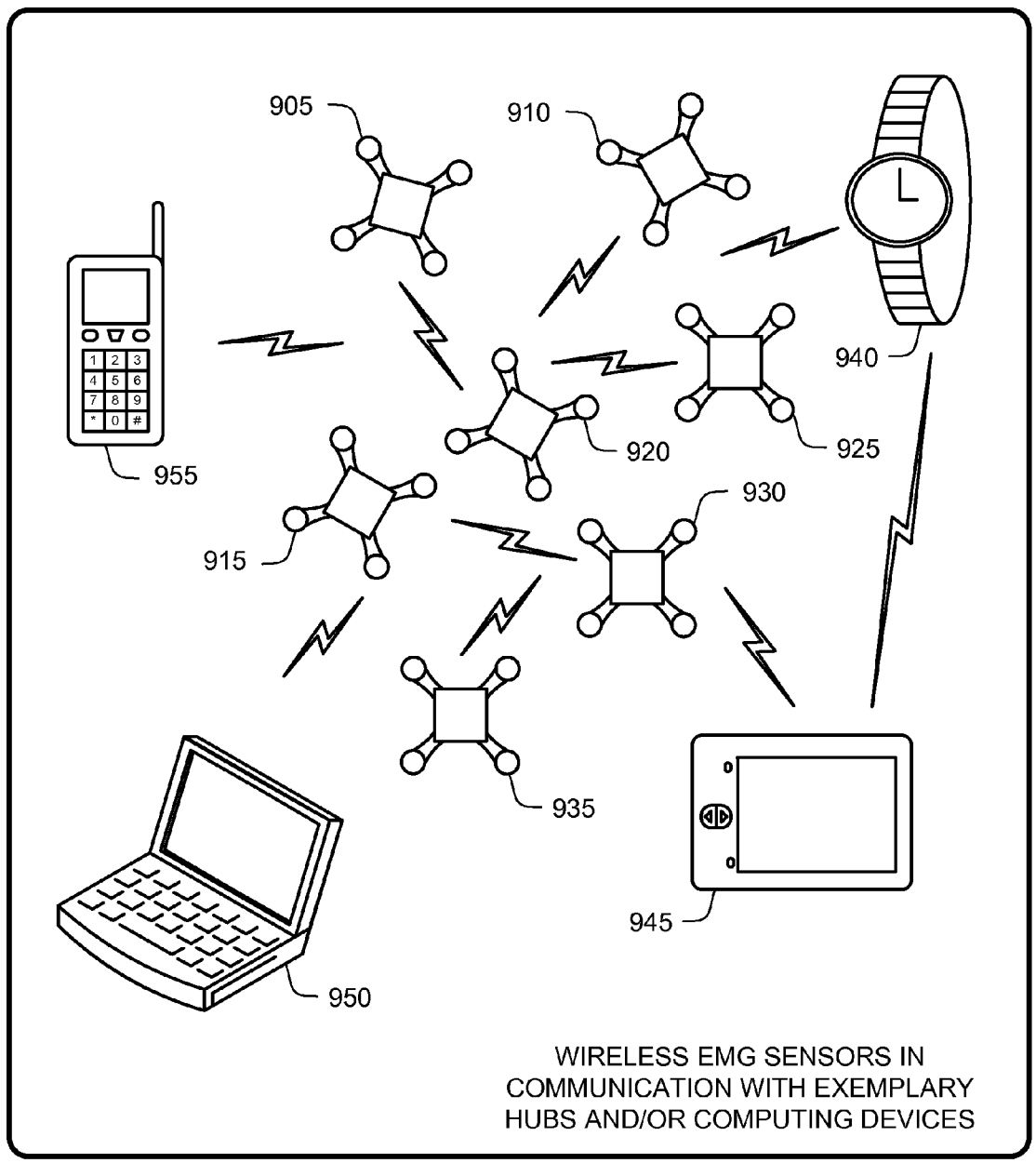
FIG. 9 illustrates the use of wireless EMG-based sensor nodes with various types of hubs and/or computing devices, for implementing various embodiments of the Wearable Electromyography-Based Controller, as described herein.

For example, FIG. 9 provides a simple diagram which illustrates a plurality of wireless sensor nodes (905, 910, 915, 920, 925, 930, and 935) acting either as individually placed sensors or as sensor nodes embedded in a device such as the armband described herein. As illustrated in FIG. 9, these wireless sensor nodes (905, 910, 915, 920, 925, 930, and 935)

are variously in communication with each other and one or more devices, including a wristwatch 940, a digital media player 945, a PC-type notebook computer 950, and a cell phone 955. Note also that FIG. 9 illustrates the wristwatch acting as a "hub" in the case, as a wireless intermediary between one or more of the sensor nodes and the digital media player 945.

Figure 10:
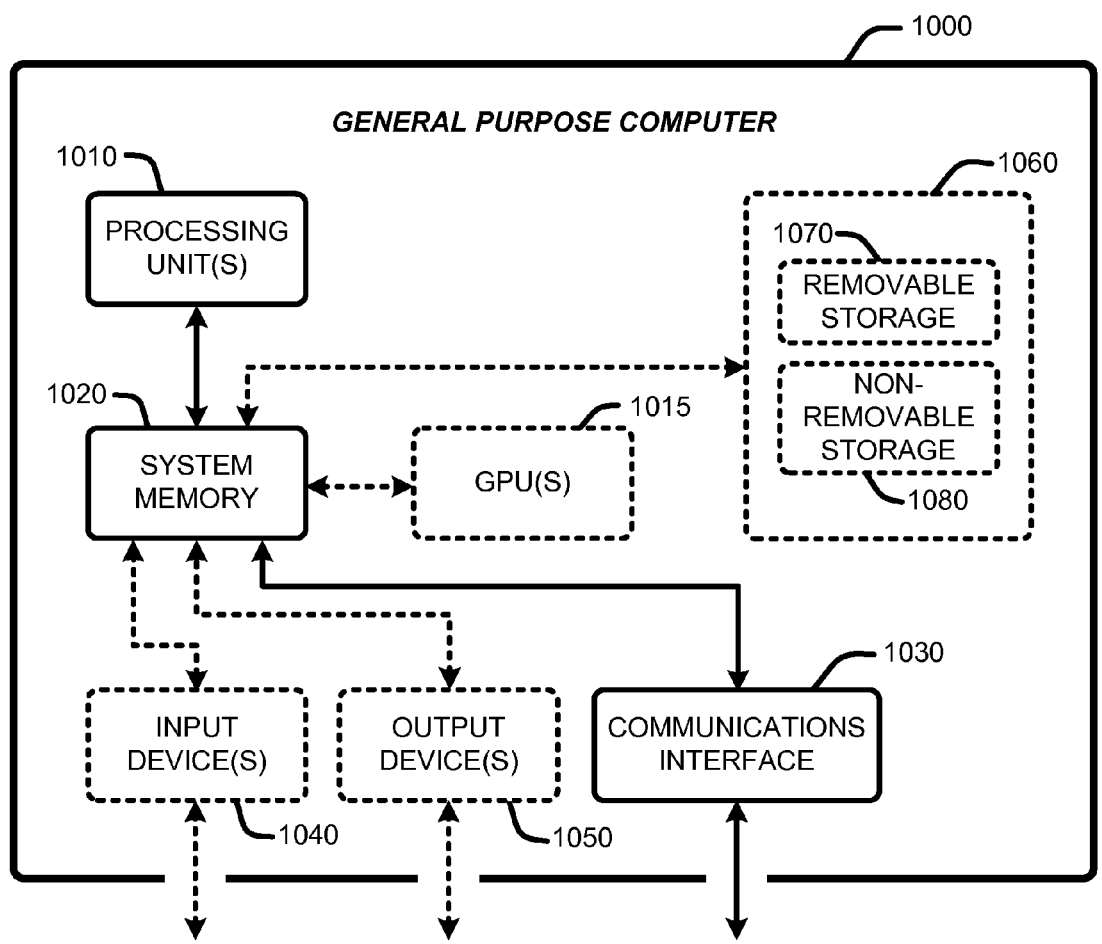
FIG. 10 is a general system diagram depicting a simplified general-purpose computing device having simplified computing and I/O capabilities for interacting with the Wearable Electromyography-Based Controller, as described herein.

FIG. 10 illustrates a simplified example of a general-purpose computer system on which various embodiments and elements of the Wearable Electromyography-Based Controller, as described herein, may be implemented. It should be noted that any boxes that are represented by broken or dashed lines in FIG. 4 represent alternate embodiments of the simplified computing device, and that any or all of these alternate embodiments, as described below, may be used in combination with other alternate embodiments that are described throughout this document.

For example, FIG. 10 shows a general system diagram showing a simplified computing device. Such computing devices can be typically be found in devices having at least some minimum computational capability, including, but not limited to, personal computers, server computers, hand-held computing devices, laptop or mobile computers, communications devices such as cell phones and PDA's, multiprocessor systems, microprocessor-based systems, set top boxes, programmable consumer electronics, network PCs, minicomputers, mainframe computers, video media players, in-vehicle computing systems (e.g., automotive computer system), etc.

As noted above, computing devices such as those described herein operate either in response to user gestures recognized via one or more Wearable Electromyography-Based Controllers. However, in various embodiments, such computing devices also provide computing power for operations such as the initial self-calibration described in Section 2.3. In addition, such computing devices may also act as hubs or intermediaries to facilitate communications between the Wearable Electromyography-Based Controller and one or more other computing devices or attached mechanisms.

In general, such computing devices include at least some minimum computational capability along with some way to send and receive data. In particular, as illustrated by FIG. 10, the computational capability is generally illustrated by one or more processing unit(s) 1010, and may also include one or more GPUs 1015. Note that that the processing unit(s) 1010 of the general computing device of may be specialized microprocessors, such as a DSP, a VLIW, or other micro-controller, or can be conventional CPUs having one or more processing cores, including specialized GPU-based cores in a multi-core CPU.

In addition, the simplified computing device of FIG. 10 may also include other components, such as, for example, a communications interface 1030. The simplified computing device of FIG. 10 may also include one or more conventional computer input devices 1040 (such as a microphone or microphone array for receiving voice inputs). The simplified computing device of FIG. 10 may also include other optional components, such as, for example one or more conventional computer output devices 1050 (such as audio and/or video output devices). Finally, the simplified computing device of FIG. 10 may also include storage 1060 that is either removable 1070 and/or non-removable 1080. Note that typical communications interfaces 1030, input devices 1040, output devices 1050, and storage devices 1060 for general-purpose computers are well known to those skilled in the art, and will not be described in detail herein.

The foregoing description of the Wearable Electromyography-Based Controller has been presented for the purposes of illustration and description. It is not intended to be exhaustive or to limit the claimed subject matter to the precise form disclosed. Many modifications and variations are possible in light of the above teaching. Further, it should be noted that any or all of the aforementioned alternate embodiments may be used in any combination desired to form additional hybrid embodiments of the Wearable Electromyography-Based Controller. It is intended that the scope of the invention be limited not by this detailed description, but rather by the claims appended hereto.

What is claimed is:

1. A human-computer interface, comprising:
    an arbitrarily positionable wearable device having a plurality of sensor nodes, wherein each sensor node further includes one or more Electromyography (EMG) sensors;
    a module for activating the wearable device following receipt of an explicit indication provided by the user;
    a module for automatically measuring muscle generated electrical signals using one or more of the EMG sensors;
    a module for automatically determining which muscle generated electrical signals correspond to one or more specific user gestures; and
    a module for causing one or more computing devices to automatically execute one or more specific commands corresponding to one or more of the specific user gestures.

2. The human-computer interface of claim 1 further comprising a calibration phase which automatically identifies one or more specific user muscles which generate the electrical signals measured by one or more specific EMG sensors.

3. The human-computer interface of claim 2 wherein the user performs one or more specific gestures as part of a training phase for the calibration.

4. The human-computer interface of claim 1 wherein a subset of the EMG sensors is identified by an automated multiplexing process which determines which EMG sensors are sufficient to measure the muscle generated electrical signals that are associated with one or more of the specific user gestures.

5. The human-computer interface of claim 4 further comprising a module for automatically disabling all EMG sensors not included in the subset of EMG sensors.

6. The human-computer interface of claim 1 further comprising a module for automatically determining an approximate position of the wearable device on the surface of the skin of the user's body.

7. The human-computer interface of claim 1 further comprising a module for automatically determining relative positions of the sensor nodes to each other.

8. The human-computer interface of claim 1 wherein the wearable device communicates wirelessly with one or more of the computing devices.

9. The human-computer interface of claim 1 further comprising a module which provides automatic feedback to the user for directing the user to refine placement of a position of the wearable device on the surface of the user's skin.

10. The human-computer interface of claim 1 further comprising a module for providing automatic feedback to the user to indicate whether one or more of the specific commands were successfully executed in response to one or more specific user gestures.

11. The human-computer interface of claim 1 further comprising a module for deactivating the wearable device following receipt of an explicit indication provided by the user.

12. A process for sending commands to one or more computing devices, comprising:
- arbitrarily positioning a wearable device in contact with an outer surface of a user's skin, said wearable device having a plurality of Electromyography (EMG) sensors for measuring muscle generated electrical activity via the skin of the user;
- performing an automated positional localization process to automatically determine an approximate position of the wearable device on the surface of the skin of the user's body;
- automatically evaluating muscle-generated electrical signals of the user measured via one or more of the EMG sensors to automatically identify one or more specific gestures of the user from a predefined set of gestures; and
- automatically directing one or more computing devices to execute one or more specific commands corresponding to one or more of the identified gestures.

13. The process of claim 12 further comprising performing an initial calibration process which evaluates muscle generated electrical signals associated with a subset of gestures to determine expected muscle generated electrical signals for the complete set of gestures.

14. The process of claim 12 wherein commands associated with one or more of the gestures of the set of gestures is user definable.

15. A system for providing a human-computer interface (HCI), comprising:
- a user-wearable device having a plurality of Electromyography (EMG) sensors, said user-wearable device being placed on an outer surface of the user's skin in an approximate position on a pre-determined body part of the user;
- an automated self-calibration process which maps muscle generated electrical signals corresponding to one or more specific user gestures to one or more specific commands, said muscle generated electrical signals being measured by one or more of the EMG sensors;
- an automated process for identifying a subset of the EMG sensors as being sufficient to measure muscle generated electrical signals to accurately identify the specific commands mapped the specific user gestures;
- an automated process for disabling all EMG sensors not included in the subset;
- an automated process for using the subset of EMG sensors to evaluating muscle generated electrical signals associated with one or more user gestures to identify the commands associated with those user gestures; and
- a process for transmitting specific commands associated with one or more specific user gestures to one or more computing devices.

16. The system of claim 15 further comprising an automated positional localization process which determines an approximate position of the user-wearable device on the body of the user.

17. The system of claim 16 further comprising an automated process for directing the user to refine the approximate position of the user-wearable device.

18. The system of claim 15 wherein the user-wearable device includes a wireless interface to one or more of the computing devices.

* * * * *